United States Patent
Hyde et al.

(10) Patent No.: US 9,872,628 B2
(45) Date of Patent: Jan. 23, 2018

(54) ELECTROCARDIOGRAM SYSTEMS AND RELATED METHODS

(71) Applicant: ELWHA LLC, Bellevue, WA (US)

(72) Inventors: Roderick A. Hyde, Redmond, WA (US); Elizabeth A. Sweeney, Seattle, WA (US)

(73) Assignee: ELWHA LLC, Bellevue, WA (US)

( * ) Notice: Subject to any disclaimer, the term of this patent is extended or adjusted under 35 U.S.C. 154(b) by 199 days.

(21) Appl. No.: 14/791,323

(22) Filed: Jul. 3, 2015

(65) Prior Publication Data
US 2017/0000370 A1   Jan. 5, 2017

(51) Int. Cl.
| | |
|---|---|
| *A61B 5/0408* | (2006.01) |
| *A61B 5/0245* | (2006.01) |
| *A61B 5/024* | (2006.01) |
| *A61B 5/06* | (2006.01) |
| *A61B 5/00* | (2006.01) |
| *A61B 8/00* | (2006.01) |

(52) U.S. Cl.
CPC ........ *A61B 5/04085* (2013.01); *A61B 5/0245* (2013.01); *A61B 5/02438* (2013.01); *A61B 5/066* (2013.01); *A61B 5/6806* (2013.01); *A61B 5/7275* (2013.01); *A61B 5/067* (2013.01); *A61B 5/684* (2013.01); *A61B 8/00* (2013.01)

(58) Field of Classification Search
None
See application file for complete search history.

(56) References Cited

U.S. PATENT DOCUMENTS

| | | | |
|---|---|---|---|
| 6,224,548 B1 | 5/2001 | Gopinathan et al. | |
| 6,248,064 B1 | 6/2001 | Gopinathan et al. | |
| 6,516,289 B2 | 2/2003 | David | |
| 6,540,673 B2 | 4/2003 | Gopinathan et al. | |
| 6,595,918 B2 | 7/2003 | Gopinathan et al. | |
| 7,112,175 B2 | 9/2006 | Gopinathan et al. | |
| 7,435,222 B2 | 10/2008 | Gopinathan et al. | |
| 7,499,745 B2 | 3/2009 | Littrup et al. | |
| 7,753,845 B2 | 7/2010 | Gopinathan et al. | |
| 9,019,106 B2* | 4/2015 | Alameh | G04G 13/023 340/573.1 |
| 2001/0000526 A1 | 4/2001 | Gopinathan et al. | |
| 2001/0051774 A1 | 12/2001 | Littrup et al. | |
| 2001/0056227 A1 | 12/2001 | Gopinathan et al. | |
| 2002/0045805 A1 | 4/2002 | Gopinathan et al. | |
| 2002/0111777 A1 | 8/2002 | David | |
| 2004/0019261 A1 | 1/2004 | Gopinathan et al. | |
| 2004/0176675 A1* | 9/2004 | Rice | A61B 5/04 600/393 |
| 2005/0075541 A1 | 4/2005 | Gopinathan et al. | |
| 2006/0229522 A1* | 10/2006 | Barr | A61B 5/0404 600/509 |

(Continued)

*Primary Examiner* — Erica Lee
(74) *Attorney, Agent, or Firm* — Dorsey & Whitney LLP

(57) ABSTRACT

Embodiments disclosed herein are directed to electrocardiogram systems and systems of using electrocardiogram systems. The electrocardiogram systems are configured to detect at least two electrical potentials (e.g., a first electrical potential and a second electrical potential) at two or more surfaces of a subject (e.g., a first surface and a second surface). In an embodiment, the electrocardiogram system includes at least one position sensor configured to detect the position of the at least one electrode relative to a surface of the subject.

54 Claims, 7 Drawing Sheets

(56) References Cited

U.S. PATENT DOCUMENTS

| | | | |
|---|---|---|---|
| 2007/0038136 A1 | 2/2007 | Gopinathan et al. | |
| 2007/0223794 A1* | 9/2007 | Preiss | A61B 8/12 382/128 |
| 2008/0171311 A1 | 7/2008 | Centen et al. | |
| 2009/0048526 A1* | 2/2009 | Aarts | A61B 5/02438 600/508 |
| 2010/0069735 A1* | 3/2010 | Berkner | A61B 5/04028 600/382 |
| 2010/0191136 A1* | 7/2010 | Wolford | A61B 5/00 600/534 |
| 2012/0088986 A1 | 4/2012 | David et al. | |
| 2012/0089054 A1 | 4/2012 | Centen et al. | |
| 2013/0131500 A1* | 5/2013 | Sharonov | A61B 90/39 600/424 |
| 2014/0131066 A1 | 5/2014 | Schumacher et al. | |
| 2014/0141052 A1 | 5/2014 | Ohrlander et al. | |
| 2014/0194722 A1* | 7/2014 | Lee | A61B 8/085 600/407 |
| 2014/0278171 A1* | 9/2014 | Kahlke | G01R 23/02 702/64 |
| 2014/0350377 A1 | 11/2014 | Liang et al. | |
| 2015/0338979 A1* | 11/2015 | Rhee | G06F 3/0414 345/174 |
| 2016/0317088 A1* | 11/2016 | Fougere | A61B 5/0478 |

\* cited by examiner

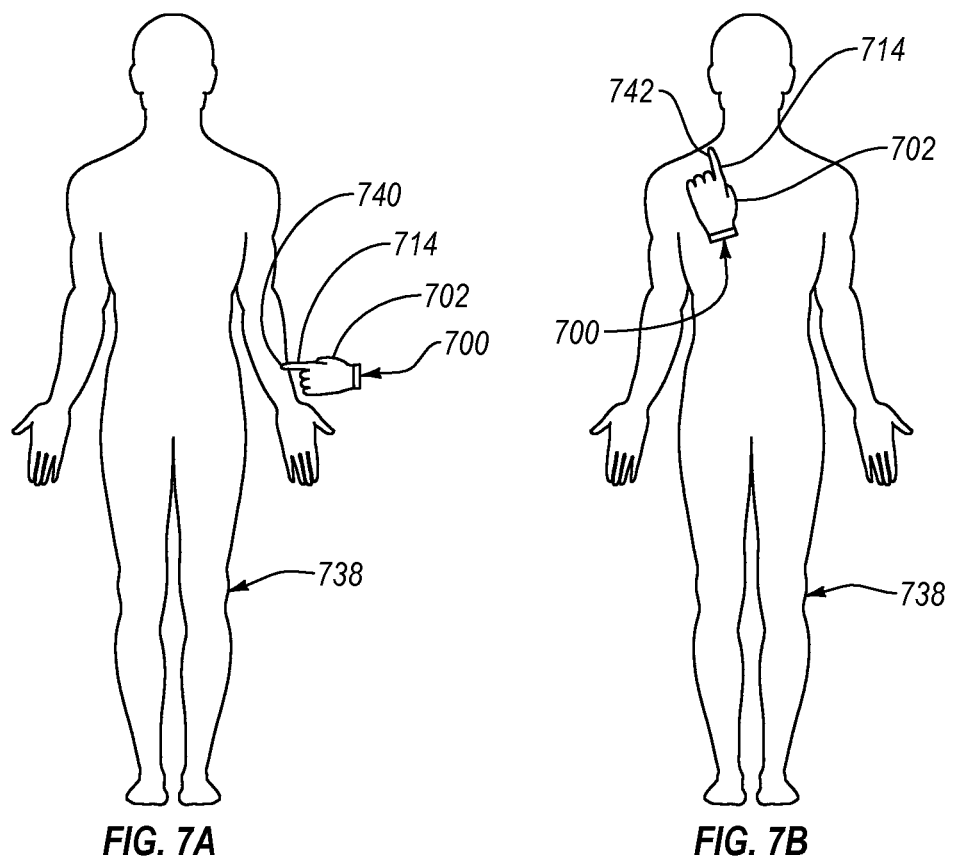
*FIG. 7A*  *FIG. 7B*

ELECTROCARDIOGRAM SYSTEMS AND RELATED METHODS

If an Application Data Sheet (ADS) has been filed on the filing date of this application, it is incorporated by reference herein. Any applications claimed on the ADS for priority under 35 U.S.C. §§119, 110, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Electrocardiogram (EKG) systems are typically utilized to detect and record electrical activity of a heart of a subject over a period of time. For example, an EKG system detects a voltage between electrical potentials detected at two or more surfaces of a subject. The voltage can measure a certain angle of the electrical axis of the heart or an anatomical area of the heart.

Typically, EKG systems are used with a 12 lead EKG. The 12 lead EKG measures voltage at twelve different angles of the electrical axis of the heart. In a conventional 12 lead EKG, ten separate and distinct electrodes are placed on ten different and specific surfaces of the subject simultaneously. Each of the ten separate and distinct electrodes are connected to a computing device. Each of the ten separate and distinct electrodes detect electrical potentials at a corresponding surface of the subject.

The computing device uses the detected electrical potentials to determine twelve different voltages. For example, the computing device can determine the three limb leads (e.g., limb I, limb II, and limb III), the three augmented limb leads (e.g., aVR, aVL, and aVF), and the six precordial leads (e.g., the voltage between the six chest electrode placements and Wilson's central terminal). The term "lead" in electrocardiography in the context of what the computing device determines refers to the 12 different vectors along which the heart's depolarization is measured and recorded.

The computing device then generates a report including a graphical representation of the voltage of each lead as a function of time. Typically, each lead has a specific location on the generated report.

SUMMARY

Embodiments disclosed herein are directed to EKG systems and methods of using EKG systems. The EKG systems are configured to detect at least two electrical potentials (e.g., a first electrical potential and a second electrical potential) at two or more surfaces of a subject (e.g., a first surface and a second surface).

In an embodiment, a method of using an EKG system is disclosed. A first surface of a subject is contacted with at least one electrode of at least one glove. With the at least one electrode, a first electrical potential is detected on the first surface of the subject. The detected first electrical potential is stored in memory. After storing the detected first electrical potential in the memory, a second surface of the subject is contacted with the at least one electrode of the at least one glove. The detected second electrical potential is stored in the memory. With a processor, a voltage is determined between the detected first electrical potential and the detected second electrical potential.

In an embodiment, a system for capturing EKG readings is disclosed. The system includes at least one glove including at least one electrode. The at least one electrode is configured to contact a first surface of a subject and detect a first electrical potential on the first surface. The at least one electrode is configured to contact a second surface of the subject and detect a second electrical potential on the second surface at some time after the first electrical potential was detected. The system further includes memory operably coupled to the at least one electrode. The memory is configured to receive and store therein the detected first electrical potential. The memory is further configured to receive and store the detected second electrical potential. The system also includes a processor operably coupled to the memory. The processor is configured to determine a voltage between the detected first electrical potential and the detected second electrical potential. The processor is further configured to generate a report including the voltage.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 7A and 7B are schematic illustrations of a method of using an EKG system to generate a report, according to an embodiment.

DETAILED DESCRIPTION

Embodiments disclosed herein are directed to EKG systems and methods of using EKG systems. The EKG systems are configured to detect at least two electrical potentials (e.g., a first electrical potential and a second electrical potential) at two or more surfaces of a subject (e.g., a first surface and a second surface). At least some of the two of the electrical potentials are detected at different times. The EKG systems can include at least one glove. The at least one glove can include at least one electrode. An individual can use the at least one glove to contact the at least one electrode against, for example, a first surface. The at least one electrode can detect a first electrical potential at the first surface. The individual can then reposition the at least one glove to contact the at least one electrode against a second surface. The at least one electrode can detect a second electrical potential at the second surface. The EKG systems can further include a controller configured to generate a report including a voltage between at least the first detected electrical potential and the second detected electrical potential. The EKG systems can further include at least one position sensor configured to detect the position of the at least one electrode 104 relative to the subject.

Figure 1:
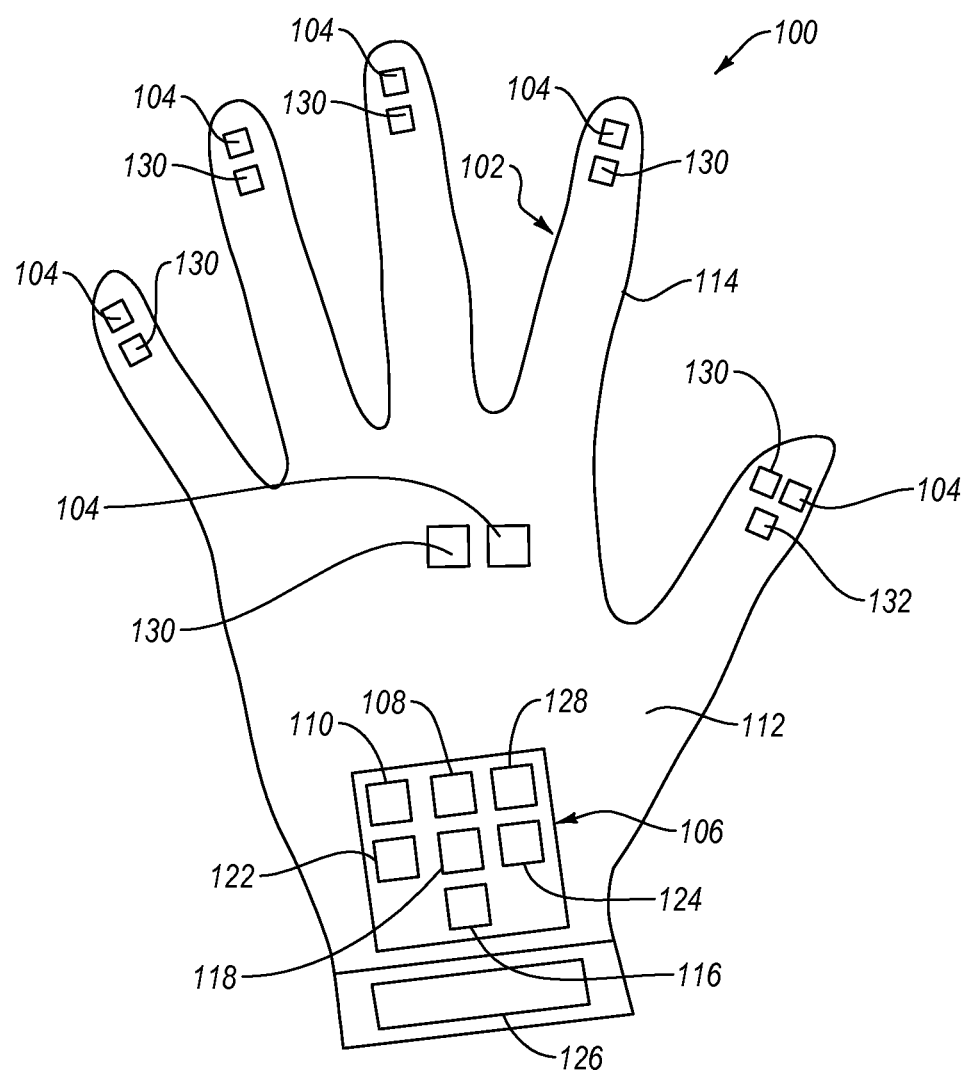
FIG. 1 is a schematic illustration of an EKG system, according to an embodiment.

FIG. 1 is a schematic illustration of an EKG system 100, according to an embodiment. The EKG system 100 is configured to capture EKG readings. The EKG system 100 includes at least one glove 102. The at least one glove 102 can include at least one electrode 104 (e.g., a single electrode 104 or a plurality of electrodes 104). The at least one electrode 104 is configured to detect two or more electrical potentials at two or more different of surfaces of a subject. At least two electrical potentials are detected at different times.

The EKG system 100 further includes a controller 106 having memory 108, a processor 110 operably coupled to the memory 108, and control electrical circuitry 116 configured to control all or some components of the EKG system 100. The controller 106 can receive data (e.g., the detected plurality of electrical potentials) from the at least one electrode 104 and stores the data in the memory 108. The processor 110 can determine a voltage (i.e., difference) between the at least two of the detected plurality of electrical potentials detected at different times.

The at least one glove 102 can be any article that is configured to be at least partially worn on a hand of an individual (e.g., a doctor, nurse, other caregiver, or subject). In an embodiment, the at least one glove 102 can be configured to be worn on only a portion of the hand of the individual (e.g., one or more fingers, the palm), the entire hand of the individual, or at least a portion of the hand and a portion of the arm of the individual extending from the hand towards a shoulder of the individual (e.g., the wrist, the forearm). In an embodiment, the at least one glove 102 can include a traditional glove (e.g., a glove having five fingers 114), a mitten, a gunner's mitten, a scratch mitt, a fingerless glove, or any other type of glove. In an embodiment, the at least one glove 102 can be made from at least one of rubber, leather, composite, a conductive material, an insulating material, a suitable fabric, or other suitable material. The at least one glove 102 can be configured to be reusable or disposable (e.g., latex glove).

The at least one glove 102 can include at least one electrode 104. The at least one electrode 104 can be configured to be electronically coupled to (e.g., detects the electrical activity) a heart of the subject. For example, the at least one electrode 104 can detect the electrical potential at a surface of the subject. The electrical potential detected by the at least one electrode 104 can include directly detecting the electrical potential at the surface or indirectly detecting the electrical potential at the surface by detecting one or more electrical characteristics of the surface that can be used to calculate the electrical potential. The detected electrical potential can provide information about the electrical depolarization of the heart during each cardiac cycle (i.e., heartbeat).

The at least one electrode 104 can include an insulated conductor. The insulated conductor can include any suitable electrical conductor such as a conductive polymer (e.g., polypyrrole), a conductive metal (e.g., copper, silver), a conductive ceramic, or a conductive composite. For example, the insulated conductor can include a flexible electrical conductor or a rigid electrical conductor. In an embodiment, the at least one electrode 104 can include a conductive material applied thereto configured to improve electrical contact between the at least one electrode 104 and a surface of the subject (e.g., a conductive gel). In an embodiment, the at least one electrode 104 can include or can be coupled to a device configured to receive one or more signals from the at least one electrode 104 (e.g., the detected electrical characteristics) and outputs usable data (e.g., the electrical potential or a digital signal). The device can be attached to the at least one electrode 104, positioned adjacent to or proximate to the at least one electrode 104, or positioned in the controller 106. In an embodiment, one of the plurality of electrodes 104 can be configured to be a neutral electrode. In an embodiment, at least one of the plurality of electrodes 104 can be configured to transmit data (e.g., the electrical potential, the usable data) to the controller 106. As such, the at least one electrode 104 can be wiredly or wirelessly coupled to the controller 106.

The at least one electrode 104 can be coupled to the at least one glove 102. In an embodiment, the at least one electrode 104 is attached to the at least one glove 102. For example, the at least one electrode 104 can be reversibly attached to the at least one glove (e.g., using Velcro). In an embodiment, the at least one electrode 104 can be at least partially enclosed in the at least one glove 102. For example, the at least one glove 102 can include one or more recesses formed therein configured to receive the one or more electrode 104. In an embodiment, the at least one electrode 104 can be completely enclosed in the at least one glove 102. For example, the at least one electrode 104 can be positioned sufficiently proximate to an exterior surface of the at least one glove 102 to detect the electrical potential of a surface of a subject when the exterior surface of the at least one glove contacts the subject.

The at least one electrode 104 can be positioned anywhere on the at least one glove 102 that enables the at least one electrode 104 to detect the electrical potential at a surface of the subject. In an embodiment, the at least one glove 102 can include at least one finger 114, such as a plurality of fingers 114. In such an embodiment, each finger 114 can include at least one electrode 104. For example, the at least one electrode 104 can be coupled to a distal phalanx, a middle phalanx, or a proximal phalanx of the at least one finger 114. In an embodiment, the at least one electrode 104 can be configured to not inhibit movement (e.g., bending) of the at least one finger 114. Not inhibiting movement of the at least one finger 114 can facilitate placement of the at least one electrode 104 on the surface of the subject. In an embodiment, the at least one electrode 104 can be coupled to a palm 112 of the at least one glove 102. In an embodiment, multiple electrodes 104 can be distributed throughout the at least one glove 102 (e.g., at least one finger 114 and the palm 112). In an embodiment, the at least one electrode 104 can be positioned on the at least one glove 102 to facilitate placement of the at least one electrode 104. For example, the at least one glove 102 can be configured to perform a typical 12 lead EKG. In such an example, the at least one glove 102 can have at least two electrodes 104 coupled thereto. The spacing between the at least two electrodes 104 can have substantially the same spacing therebetween as two chest electrode placements (e.g., $V_1$, $V_2$, $V_3$, $V_4$, $V_5$, or $V_6$). As such, the EKG system 100 can detect two electrical potentials at two chest electrode placements substantially simultaneously.

In an embodiment, the at least one electrode 104 can be configured to detect electrical potentials at certain times. For example, the at least one electrode 104 can be configured to detect an electrical potential when the at least one electrode 104 contacts a surface of the subject. Alternatively, the at least one electrode 104 can detect an electrical potential responsive to direction from the control electrical circuitry 116. Additionally, the at least one electrode 104 can be configured to detect electrical potentials for certain time intervals. For example, the at least one electrode 104 can be configured to detect the electrical potential for as long as the at least one electrode 104 contacts the surface. Alternatively, the at least one electrode 104 can detect the electrical potential for a certain time interval, such as for about 1 second or more, about 1 heartbeat or more, about 4 seconds or more, about 6 heartbeats or more, about 10 second or more, about 10 heartbeats or more, or about 30 seconds or more. The time interval can be the same or different for at least some of the electrical potentials detected by the at least one electrode 104. The at least one electrode 104 can detect the electrical potential for a preset time interval or responsive to direction from the control electrical circuitry 116.

In an embodiment, the at least one electrode 104 can include a plurality of electrodes 104 configured to act in unison. For example, at least some of the plurality of electrodes 104 can be configured to detect electrical potentials at one or more surfaces substantially simultaneously. Alternatively, at least some of the plurality of electrodes 104 can be configured to detect electrical potentials at one or more surfaces substantially non-simultaneously, such as in a sequential order. For example, detecting a first electrical potential at a first surface with a first electrode 104 can cause electrical interference that affects a second electrical potential detected at a second surface by a second electrode 104. In an embodiment, the at least one electrode 104 can include a plurality of electrodes 104 configured to not act in unison. For example, each of the plurality of electrodes 104 can detect an electrical potential at a surface when each electrode 104 contacts the surface. In an embodiment, the plurality of electrodes 104 can act in unison or not responsive to direction from the control electrical circuitry 116.

The at least one electrode 104 is configured to detect electrical potentials at two or more surfaces of the subject at different times. For example, the at least one glove 102 is positioned to contact the least one electrode 104 against a first surface of the subject. The at least one electrode 104 then detects a first electrical potential at the first surface. After detecting the first electrical potential, the at least one glove 102 is repositioned to contact the at least one electrode 104 against a second surface of the subject. The second surface can be adjacent to, proximate to, or distinct from the first surface of the subject. For example, the second surface can be located on a distinctly different portion of the subject than the first surface. The at least one electrode 104 can detect a second electrical potential at a second surface of the subject. In an embodiment, the at least one glove 102 can then be positioned to contact the at least one electrode 104 against one or more additional surfaces of the subject (e.g., a third surface) and detects a corresponding one or more additional electrical potentials (e.g., a third electrical potential). In an embodiment, the at least one electrode 104 can detect the plurality of electrical potentials responsive to direction from the control electrical circuitry 116.

In an embodiment, the at least one electrode 104 can be configured to detect a plurality of electrical potentials at a single surface. For example, the at least one glove 102 can be positioned to contact the at least one electrode 104 against a surface of the subject (e.g., a first surface, a second surface). The at least one electrode 104 can then detect a plurality of electrical potentials (e.g., a plurality of first electrical potentials, a plurality of second electrical potentials) at the surface. The at least one electrode 104 can detect each of the plurality of electrical potentials at different times. For example, the at least one electrode 104 can detect a subsequent electrical potential immediately after an antecedent electrical potential is detected. In an embodiment, the at least one electrode 104 can detect a subsequent electrical potential at some time period after an antecedent electrical potential stops being detected. For example, the at least one glove 102 can detect an initial antecedent first electrical potential at the first surface of the subject. The at least one glove 102 can then be positioned to contact the at least one electrode 104 against one or more additional surfaces and detects a corresponding one or more electrical potentials. The at least one glove 102 can then be positioned to contact the at least one electrode 104 against the first surface again. The at least one electrode 104 can then detect a subsequent electrical potential at the surface. In an embodiment, the at least one electrode 104 can detect each of the plurality of first electrical potentials for a certain time interval. The time interval can be the same for each of the plurality of electrical potentials, the same for at least some of the plurality of electrical potentials, or different for each of the plurality of electrical potentials. In an embodiment, the at least one electrode 104 detects the plurality of electrical potentials at the single surface responsive to direction from the control electrical circuitry 116.

As discussed above, the EKG system 100 include the controller 106. At least a portion of the controller 106 can be attached to or at least partially positioned within remote from the at least one glove 102. In an embodiment, the controller 106 can include a receiver 118 configured to receive information from one or more sources. For example, the receiver 118 can also be communicably coupled, either directly or indirectly, to one or more components of the controller 106, such as the at least one electrode 104. In an embodiment, the receiver 118 can be configured to receive information from one or more sources located remote from the at least one glove 102. For example, the receiver 118 can be configured to receive one or more telecommunications through a Wi-Fi network, a cellular network, or any suitable communication system. Such configurations can enable the EKG system 100 to receive instructions from an individual or system that is located remote from the at least one glove 102 (e.g., telemedicine).

The memory 108 can include random access memory (RAM), read only memory (ROM), a hard drive, a disc (e.g., blue-ray, DVD, or compact disc), flash memory, other types of memory electrical circuitry, or other suitable memory. In an embodiment, the memory 108 can be configured to store detected electrical potentials. The memory 108 can receive the electrical potentials directly from the at least one electrode 104 or indirectly through the receiver 118. The at least one electrode 104 can transmit a detected electrical potential while detecting the electrical potential or after the at least one electrode 104 detects the electrical potential. In an embodiment, the at least one electrode 104 can detect a plurality of electrical potentials. The at least one electrode can transmit at least some of the detected plurality of electrical potentials to the memory 108. In an embodiment, the memory 108 can be communicably coupled to one or more components of the EKG system 100 and can be configured to transmit the detected electrical potentials stored therein to any of the one or more components coupled thereto (e.g., the processor 110).

In an embodiment, the memory 108 can further include operational instructions for operating the EKG system 100 stored therein. The instructions stored on the memory 108 can include programs configured to determine a voltage from two detected electrical potentials, programs configured to adjust data associated with at least one detected electrical potential, information about the EKG system 100, or additional information.

In an embodiment, the processor 110 can be operably coupled to the memory 108. For example, the processor 110 can be configured to receive information (e.g., from the memory 108) and process the information according to instructions contained on the memory 108. In an embodiment, the processor 110 can receive one or more electrical characteristics detected by the at least one electrode 104 from the memory 108. The processor 110 can then calculate an electrical potential using the one or more electrical characteristics. In an embodiment, the processor 110 can be configured to adjust one or more detected electrical potentials. For example, the at least one electrode 104 can detect a first electrical potential at a first surface when the subject has a first heart rate. Then, the at least one electrode 104 can detect a second electrical potential at a second surface when the subject has a second heart rate. The first heart rate and the second heart rate can be different. In another example, the at least one electrode 104 can contact the first surface of the subject and can start detecting the first electrical potential at a first portion of the heartbeat (e.g., during the repolarization of the ventricles). Then, the at least one electrode 104 can contact the second surface of the subject and start detecting the second electrical potential at the second surface at a second portion of the heartbeat (e.g., during the depolarization of the atria). The first portion of the heartbeat can be different than the second portion of the heartbeat. In both examples, the processor 110 can adjust the data associated with the detected first electrical potential or the detected second electrical potential to compensate for the differences. For example, the processor 110 can adjust the data associated with the detected first electrical potential or the detected second electrical potential such that the first heat rate and the second heart rate substantially the same. In another example, the processor 110 can adjust the data associated with the detected first electrical potential or the detected second electrical potential such that the first portion of the heartbeat and the second portion of the heartbeat are substantially the same.

In an embodiment, the processor 110 can be configured to directly compare at least two detected electrical potentials (e.g., the detected first electrical potential and the detected electrical potential) to generate a report. For example, the processor 110 can determine the voltage between the detected first electrical potential and the detected second electrical potential. The processor 110 can also determine the voltage as a function of time. For example, the processor 110 can generate a graphical representation of the voltage versus time (e.g., the graphical representation 534). In an embodiment, the processor 110 can determine the angle relative to the heart's electrical axis (angle) measured by the voltage (e.g., using the hexaxial reference system). In an embodiment, the processor 110 can determine the anatomical area of the heart measured by the voltage (e.g., the inferior surface of the heart, the lateral wall of the left ventricle of the heart, the septal surface of the heart, the anterior wall of the right or left ventricles).

In an embodiment, the processor 110 can be configured to determine a composite electrical potential and determine the voltage between the composite electrical potential and a detected electrical potential that was not used to determine the composite electrical potential. The composite electrical potential is an average electrical potential between at least two different detected electrical potentials. A composite electrical potential enables the EKG system 100 to detect the electrical activities of the heart at different angles or at different anatomical areas. For example, the at least one electrode 104 detects a first electrical potential at a first surface of the subject, a second electrical potential at a second surface of the subject, and a third electrical potential at a third surface of the subject. The processor 110 can average the detected second electrical potential and the detected third electrical potential to determine a composite electrical potential. The processor 110 can then determine a voltage between the detected first electrical potential and the composite electrical potential. In another example, the composite electrical potential can be calculated from an average of the detected first electrical potential with either the detected second electrical potential or the detected third electrical potential. In an embodiment, the processor 110 can determine a hypothetical composite surface. The hypothetical composite surface is hypothetical surface on which the at least one electrode 104 would have detected the composite electrical potential. The hypothetical composite surface can be located on the surface of the subject, below the surface of the subject, or above the surface of the subject. The hypothetical composite surface can be used to determine the angle or anatomical area of the heart measure by the voltage between a detected electrical potential and a composite electrical potential.

In an embodiment, the processor 110 can analyze a plurality of electrical potentials detected at a single surface. For example, the at least one electrode 104 can detect a plurality of electrical potentials (e.g., a plurality of first electrical potentials, a plurality of second electrical potentials) at a single surface of the subject (e.g., a first surface, a second surface). The processor 110 can select an antecedent electrical potential and a subsequent electrical potential from the detected plurality of electrical potentials. The at least one electrode 104 can detect an antecedent electrical potential at an antecedent time and can detect the subsequent electrical potential at a subsequent time, where the antecedent time is before the subsequent time. The processor 110 can use the antecedent first electrical potential and the subsequent first electrical potential to predict an interpolated electrical potential. The interpolated electrical potential can be a predicted electrical potential detected at a target time, where the target time is at some time between the antecedent time and the subsequent time. In an embodiment, the processor 106 or an individual can select a target time having an association with another time. The another time can be when the at least one electrode 104 detected another electrical potential at another surface. The detected another electrical potential can be an actually detected electrical potential (e.g., a third electrical potential), a composite electrical potential, or another predicted (i.e., interpolated) electrical potential detected at another target time. The target time can be substantially the same as, at some interval before, or some interval after the another time, such as a specified number of heartbeats before or after the another time. The specified number of heartbeats can be specified by the processor 110 or an individual using the EKG system 100.

In an embodiment, the processor 110 can use the detected first electrical potential (e.g., the plurality of first electrical potentials, the interpolated first electrical potential), the detected second electrical potential (e.g., the plurality of second electrical potentials, the interpolated second electrical potential), or the voltage between the detected first electrical potential and the detected second electrical potential to determine a heartbeat or heart rate of the heart of the subject. For example, the processor 110 can compare a maxima of the P waves, the R waves, or the T waves, or a minima of the Q wave, or the S wave to determine a heartbeat or heart rate. In an embodiment, the heart rate can vary. In such an embodiment, the processor 110 can determine an average heart rate during a period of time or the heart rate as a function of time.

In an embodiment, the processor 110 can use historical data of the subject or population data to generate the report. Historical data of the subject can include information or data obtained using equipment other than the EKG system 100 or obtained previously using the EKG system 100. The population data can include information (e.g., medical information) obtained from one or more individuals who share a common link with the subject. The common link can be a geographical link, an ethnic link, a genetic link, a familial link, or any other suitable link. The historical data of the subject or the population data can be used to assist an individual (e.g., a doctor) interpret the report. The historical data of the subject or the population data can be used to determine at least one characteristic of the heart of the subject. For example, the report can include a graphical representation of a voltage generated by the processor using two detected electrical potentials, the voltage measuring a certain angle or anatomical area of the heart. The report can also include population data including a graphical representation of a voltage of a person (e.g., a healthy person or a person having a heart condition), the voltage measuring a substantially similar angle or anatomical area of the heart. In another example, the report can include historical data of the subject including graphical representations of previous electrocardiograms performed on the subject.

In an embodiment, the processor 110 can use the historical data of the subject or the population data to estimate an electrical potential (i.e., an undetected electrical potential) of one or more unmeasured surfaces of the subject. For example, an individual using the EKG system 100 may be unable to detect an electrical potential at a surface due to a wound, clothing, bad electrical connections, system error, user error, or artifacts. As such, an electrical potential can be derived from the historical data of the subject or the population data and can be used as an estimated (e.g., an undetected electrical potential) of the unmeasured surface. In an embodiment, the processor 110 can use the historical data of the subject or the population data to determine the quality of data. For example, the processor 110 can compare the determined voltage against the historical data of the subject or the population data to determine if the data used to determine the voltage is good data or bad data.

In an embodiment, the controller 106 can include a transmitter 122. The transmitter 122 can be configured to transmit one or more signals from the controller 106. The one or more signals can include the report generated by the processor 110, directions from the control electrical circuitry 116, status reports, etc. In an embodiment, the transmitter 122 and the receiver 118 can be the same and integrated as a transceiver. For example, the controller 106 can include an antenna that acts as both the receiver 118 and the transmitter 122. In an embodiment, the transmitter 122 can be configured to transmit the one or more signals to an individual or system that is remote from the at least one glove 102. For example, the transmitter 122 can be configured to transmit the one or more signals using a Wi-Fi network, a cellular network, or any other suitable means of communication. In such an example, the transmitter 122 can enable the EKG system 100 to be used in telemedicine.

In an embodiment, the controller 106 can include a user interface 124 that enables an individual to communication with the EKG system 100, or vice versa. The user interface 124 can include a display, mouse, keyboard, microphone, speaker, or any other device that enables an individual and the EKG system to communicate with each other. For example, the user interface 124 can enable the individual to enter the times when the at least one electrode 104 detects electrical potentials, the historical data of the patient or the population data, etc. In an embodiment, the user interface 124 can include a display 126 coupled to the at least one glove 102. The display 126 can provide information to an individual, such as the report, the quality of the electrical contact between a surface of the subject and the at least one electrode 104, or any other suitable information. The display 126 can also enable the individual to communicate with the EKG system 100. For example, the display 126 can include a touch screen or one or more buttons.

As previously discussed, the controller 106 can include the control electrical circuitry 116. In an embodiment, the control electrical circuitry 116 controls one or more components of the EKG system 100 responsive to programming and instructions stored on the memory 108 or received from the user interface 124. In an embodiment, the control electrical circuitry 116 controls one or more components of the EKG system 100 responsive to direction from one or more components of the controller 106 (e.g., processor 110). In an embodiment, the control electrical circuitry 116 controls one or more components of the EKG system 100 responsive to instructions or programming contained within the control electrical circuitry 116. The control electrical circuitry 116 can be integrally formed with the memory 108 and the processor 110 of the controller 106. Alternatively, the control electrical circuitry 116 can be separate from the memory 108 and the processor 110 or the controller 106. In such an embodiment, the control electrical circuitry 116 can include its own memory and a processor.

In an embodiment, the controller 106 can include a power source 128. The power source 128 can be configured to provide electrical power to one or more components of the EKG system 100. In an embodiment, the power source 128 can include a cord extending therefrom that includes an electrical plug. In an embodiment, the power source 128 can include at least one battery, capacitor, photovoltaic, thermal electric generator, or any other suitable power source. The power source 128 can be rechargeable, such as wiredly or wireless rechargeable, or replaceable.

Figure 2:
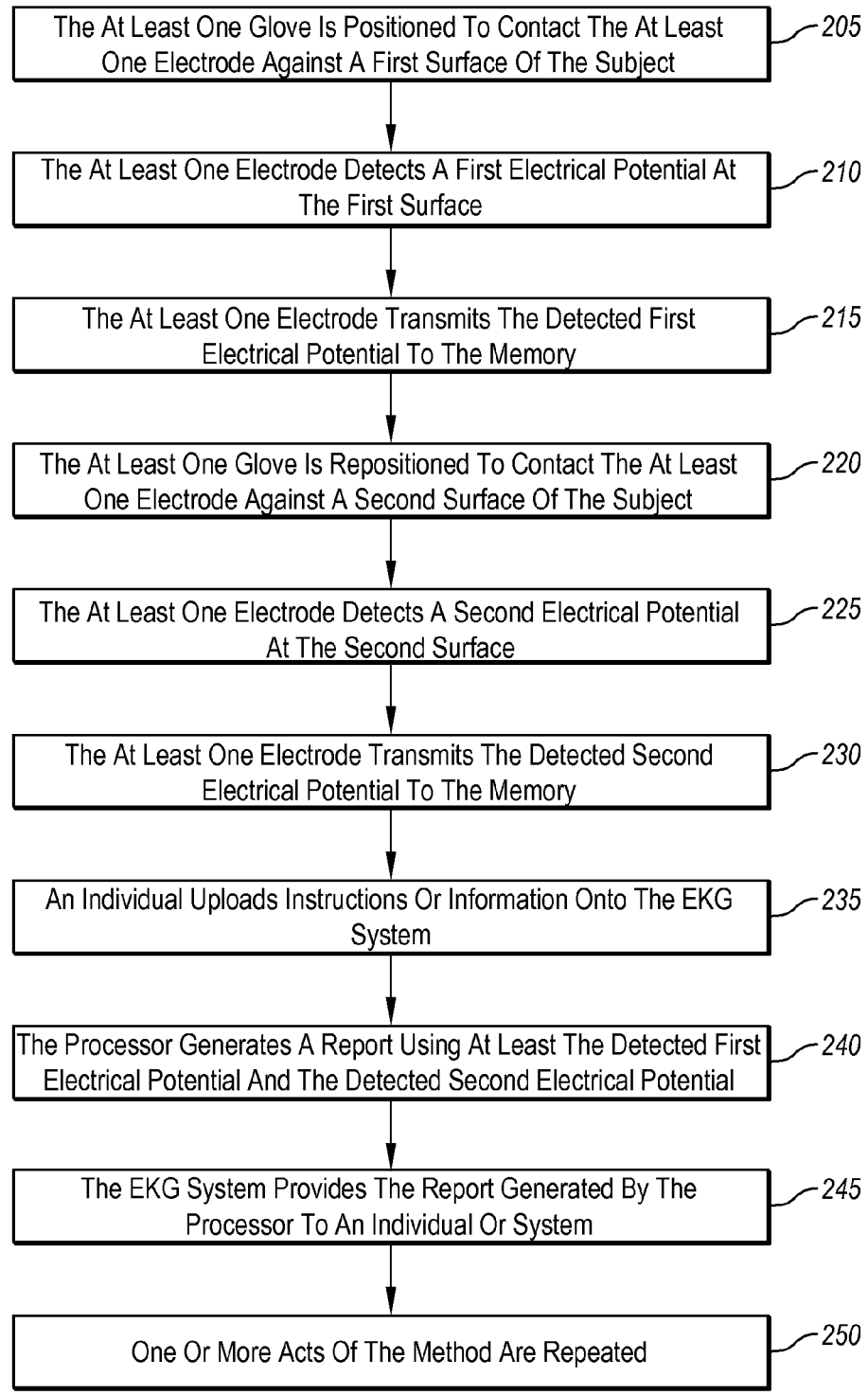
FIG. 2 is a flow diagram of a method of using the EKG system shown in FIG. 1, according to an embodiment.

FIG. 2 is a flow diagram of a method 200 of using the EKG system 100 shown in FIG. 1, according to an embodiment. The acts of the method 200 can be performed in any order. In an embodiment, some of the acts of the method 200 can be split into a plurality of acts, some of the acts can be combined into a single step, or some acts can be omitted. Also, it should be understood that additional acts can be added to the method 200. For example, additional acts can be used to operate other EKG systems disclosed herein.

Generally, in a method according to one or more embodiments, a first surface of a subject is contacted with at least one electrode of at least one glove. With the at least one electrode, a first electrical potential is detected on the first surface of the subject. The detected first electrical potential is stored in memory. After storing the detected first electrical potential in the memory, a second surface of the subject is contacted with the at least one electrode of the at least one glove. The detected second electrical potential is stored in the memory. With a processor, a voltage is determined between the detected first electrical potential and the detected second electrical potential.

Referring now to FIG. 2, in act 205, the at least one glove 102 can be positioned to contact the at least one electrode 104 against a first surface of the subject. A conductive gel or similar material can be applied to the at least one electrode 104 or the first surface prior to contacting the at least one electrode 104 against the first surface. In an embodiment, the at least one glove 102 includes a plurality of electrodes 104. In such an embodiment, one or more of the plurality of electrodes 104 can contact one or more surfaces of the subject. For example, at least one of the plurality of electrodes 104 can contact the first surface.

In act 210, the at least one electrode 104 can detect a first electrical potential at the first surface. For example, the at least one electrode 104 can directly detect the first electrical potential or one or more electrical characteristics of the first surface. In an embodiment, the at least one electrode 104 detects a plurality of first electrical potentials at the first surface. In an embodiment, the at least one glove 102 includes a plurality of electrodes 104. At least one of the plurality of electrodes 104 contacts the first surface of the subject and remaining electrodes 104 contact at least one other surface of the subject. The plurality of electrodes 104 can detect corresponding electrical potentials substantially simultaneously or non-simultaneously. In an embodiment, the at least one electrode 104 can detect the first electrical potential at the first surface responsive to direction from the control electrical circuitry 116.

In act 215, the at least one electrode 104 can transmit the detected first electrical potential to the memory 108. The at least one electrode 104 can transmit the detected first electrical potential while detecting, immediately after detecting, or at some time period after detecting the first electrical potential. In an embodiment in which the at least one electrode 104 detects a plurality of first electrical potentials, the at least one electrode 104 can transmit at least some of the plurality of first electrical potentials to the memory 108. The at least one electrode 104 transmits the detected first electrical potential directly or indirectly (e.g., via the receiver 118) to the memory 108. In an embodiment, the at least one electrode 104 transmits the detected first electrical potential to the memory 108 responsive to direction from the control electrical circuitry 116.

In act 220, the at least one glove 102 can be repositioned to contact the at least one electrode 104 against a second surface of the subject. The second surface can be adjacent to, proximate to, or distinct from the first surface of the subject. For example, the second surface can be on a distinctly different body part of the subject than the first surface. In an embodiment, the at least one glove 102 is repositioned after the at least one electrode 104 transmits the detected first electrical potential to the memory 108. Alternatively, the at least one glove 102 is moved and positioned after the at least one electrode 104 detects the first electrical potential but before the at least one electrode 104 transmits the first electrical potential to the memory 108. A conductive gel or similar material can be applied to the at least one electrode 104 or the second surface prior to contacting the at least one electrode 104 against the second surface. In an embodiment, the at least one glove 102 includes a plurality of electrodes 104. In such an embodiment, at least one of the plurality of electrodes 104 contacts the second surface.

In act 225, the at least one electrode 104 can detect a second electrical potential at the second surface. The at least one electrode 104 can detect the second electrical potential in substantially the same manner as described in act 210. In act 230, the at least one electrode 104 can transmit the detected second electrical potential to the memory 108. The at least one electrode 104 can transmit the detected second electrical potential to the memory 108 in substantially the same manner as described in act 215

In act 235, an individual can optionally upload instructions or information onto the EKG system 100. For example, the individual can upload historical data of the subject or population data. In an embodiment, the individual can upload the position of the first surface or the second surface relative the subject. In an embodiment, the individual can upload instructions to execute a program, or any other suitable instruction.

In act 240, the processor 110 can generate a report using at least the detected first electrical potential and the detected second electrical potential. The report can include a graphical representation of the voltage between the detected first electrical potential and the detected second electrical potential as a function of time. In an embodiment, the processor 110 can compare the detected first electrical potential or the detected second electrical potential with a composite electrical potential, an interpolated electrical potential, historical data of the subject, or population data. In an embodiment, the processor 110 can adjust the detected first electrical potential or the detected second electrical potential. In an embodiment, the processor 110 can use the location of the first surface or the second surface relative the subject to determine the angle or anatomical area of the heart measured by the voltage.

In act 245, the EKG system 100 can provide the report generated by the processor 110 to an individual or system. For example, the EKG system 100 can transmit the report to the user interface 124 which displays the report using the display 126. Alternatively, the EKG system 100 can transmit the report via a telecommunication network.

In act 250, one or more acts of the method 200 can be repeated. For example, acts 220 to 230 can be repeated to determine one or more additional electrical potentials (e.g., a third electrical potential) detected at one or more additional surfaces of the subject (e.g., a third surface).

Referring back to FIG. 1, in an embodiment, the EKG system 100 can include one or more components configured to facilitate placement of the at least one electrode 104 on a suitable surface of the subject. For example, the EKG system 100 facilitates placement of the at least one electrode 104 on surfaces that enable the EKG system 100 to determine a voltage that measures a certain angle or anatomical area of the heart. In an embodiment, the EKG system 100 facilitates placement of the at least one electrode 104 on a surface that minimizes or prevents artifacts (e.g., electrical activity caused by something other than the heart).

In an embodiment, the EKG system 100 can include one or more cords (not shown) extending between at least two fingers 114 of the at least one glove 102. The one or more cords can be a flexible, semi-flexible, or rigid cord. The one or more cords can be configured to ensure that the at least two fingers 114 of the at least one glove 102 have certain spacing therebetween. In an embodiment, one or more portions of the at least one glove 102 can be semi-rigid or rigid. The semi-rigid or rigid portion of the at least one glove 102 can be configured to ensure correct spacing between the at least two fingers 114.

In an embodiment, the EKG system 100 can include at least one position sensor 130. The at least one position sensor 130 can be configured to detect one or more positions of at least one electrode 104 relative to the subject. In an embodiment, the at least one position sensor 130 can be coupled to the at least one glove 102 such that the at least one position sensor 130 has a known position relative to at least one electrode 104. For example, the at least one position sensor 130 can be positioned immediately adjacent to or spaced from the at least one electrode 104. In an embodiment, each position sensor 130 has a known position relative to a single electrode 104 or a plurality of electrodes 104. In an embodiment, a plurality of position sensors 130 can have a known location relative to a single electrode 104. For example, a first position sensor 130 can be configured to detect the position of the single electrode 104 relative to a surface feature (e.g., skin) of the subject, while a second position sensor 130 can be configured to detect the position of the single electrode 104 relative to a subsurface feature (e.g., bone, muscle, blood vessels, etc.) of the subject.

In an embodiment, the at least one position sensor 130 can include any position sensor configured to detect the position of the at least one electrode 104 relative to the subject. The at least one position sensor 130 can include one or more of an accelerometer, a topography sensor, an optical sensor, an acoustic sensor, a contact sensor, a micro-impulse radar, or any other sensor suitable for collecting data related to the position of the at least one glove 102 or a discrete portion thereof. For example, the at least one position sensor 130 can include at least one accelerometer configured to detect the relative movement or orientation (e.g., direction of tilt or direction that the at least one glove 102 is facing) of the at least one glove 102 or a discrete portion thereof over time, such as from a first time to a second time. The accelerometer can be configured to determine the relative orientation of the at least one glove 102 or a discrete portion thereof. In an embodiment, more than one accelerometer can be used on the at least one glove 102 including at least one accelerometer for determining changes in relative position and at least one accelerometer for determining the relative orientation of the at least one glove 102 or a discrete portion thereof. When the starting position of the at least one glove 102 or a portion thereof is known, the subsequent position of the at least one glove 102, with respect to a subject, can be determined using only the movement and orientation information collected from the at least one accelerometer. For example, the controller 106 can relate any measured movement and orientations from the starting position in a chronological order to determine a route and final destination of the at least one glove 102 over a period of time. In an embodiment, the at least one accelerometer can be configured to determine the acceleration or velocity of the at least one glove 102 or a portion thereof (e.g., an electrode) at the time of measuring the electrical potential at a location on a subject, and transmit the same to the controller 106. The controller 106 can be used to determine if the at least a portion of the at least one glove 102 was moving at a velocity, or accelerating below a threshold velocity or acceleration at the time that one or more measurements (e.g., electrical potential measurements or positional measurements) were made. In instances in which the at least one glove 102 or a portion thereof moving faster than a threshold velocity or a threshold acceleration, the controller 106 can tag or otherwise indicate that such measurements (e.g., electrical potential or acoustic measurements) were made at too high of a velocity or acceleration to ensure reliable results. In instances in which the at least one glove 102 was making insufficient contact with the subject when the measurement was taken, the controller 106 can tag or otherwise indicate that such measurements were made with insufficient contact and delete or otherwise segregate such data from calculations or determinations. For example, in an embodiment, the controller 106 can be configured to delete from the memory 108 all measurements taken when the corresponding velocity is about 2 millimeters per second (mm/s) or more, such as about 4 mm/s, about 8 mm/s, about 10 mm/s to about 50 mm/s, or about 10 mm/s. Similar operations can be carried out with acceleration data. For example, only measurements taken when the acceleration of the accelerometer is below about 9.8 m/s$^2$, such as about 8 m/s$^2$, about 5 m/s$^2$, or about 2 m/s$^2$ can be stored in the memory or tagged.

In an embodiment, the at least one position sensor 130 can include a topography sensor configured to sense the topography of the skin of the subject. For example, the topography sensor can include a video camera or infrared camera configured to capture one or more images of the skin of the subject. The captured video or infrared images of the topography of the skin of the subject can be transmitted to the controller 106 (e.g., the memory 108) wherein the images can be compared to a topographical atlas (e.g., an atlas including one or more reference images of the physiological features or biological structures capable as serving as references points of the subject or general demographic) or database of reference images to determine a relative position via a match between the topographical features in the captured images and the topographical atlas or database of reference images.

In an embodiment, the at least one position sensor 130 can include an optical sensor. The optical sensor can include an imaging sensor, such as a video camera or a near infrared sensor, configured to collect infrared image data of the position of one or more biological features of a subject (e.g., bones, subsurface blood vessels, muscles, etc.). The infrared sensor can be specifically configured to capture images of blood vessels or other biological features of the subject. The infrared sensor can transmit the infrared image data to the controller 106. The controller 106 can be used to determine a correlation between the collected infrared images and previously collected images or an anatomical atlas (e.g., atlas including one or more reference images of physiological features or biological structures capable as serving as references points, specific to the subject or a general demographic) to determine a match or proximity to a match of anatomical structures in the images and atlas to the relative position of the at least one glove 102 at a point in time. For example, the reference images of the atlas can include one or more reference images of the blood vessels (e.g., blood vessel reference images) of the subject or a general demographic and the captured images of the blood vessel can be compared to the blood vessel references images to determine a match in position therebetween, such as by the controller 106 or processor 110 therein.

In an embodiment, the at least one position sensor 130 can include an acoustic sensor configured to collect acoustic data (e.g., acoustic images) of the position of one or more biological structures of the subject. The acoustic sensor can include an ultrasonic (ultrasound) sensor or receiver configured to collect ultrasonic data (e.g., ultrasound/ultrasonic images) of the position of one or more biological structures of the subject. The ultrasonic sensor can transmit ultrasonic data to the controller 106. The controller 106 can be used to determine a correlation between the collected ultrasonic data and previously collected data or the anatomical atlas (e.g., reference ultrasonic images) to determine a match or proximity to a match of anatomical structures in the images to determine the relative position of the at least one glove 102 at a point in time.

In an embodiment, the at least one position sensor 130 can include an audio sensor configured to detect audio indications of heart beat or blood flow of the subject. For example, the audio sensor can include a sound detector or microphone configured to detect heart beat or can include an ultrasound Doppler sensor to detect blood flow in the subject. The sound detector can be configured to detect and record heart beat data or blood flow data which can be transmitted to the controller 106. The heart beat data or blood flow data can be used to correlate the recording position by comparison to previously recorded or known data corresponding to a particular position.

In an embodiment, the at least one position sensor 130 can include a micro-impulse radar. The micro-impulse radar can be configured to collect data of the position of one or more of external surface structures (e.g., one or more contours of the skin) or internal (subsurface) structures (e.g., bone, muscle, vessels, etc.) of a subject relative to the at least one electrode 104 or the micro-impulse radar. The micro-impulse radar can transmit the micro-impulse radar data to the controller. The controller 106 can be used to determine a correlation between the collected micro-impulse radar data and previously collected data (e.g., one or more images) or the anatomical atlas to determine a match or proximity to a match of anatomical structures in the images to determine the relative position of the at least one glove 102 at a point in time.

In an embodiment, the at least one position sensor 130 can include one or more contact sensors. The one or more contact sensors can include any one of a pressure sensor (e.g., piezoelectric sensor), and electro-magnetic sensor, a piezoresistive sensor, a capacitive sensor, an elastoresistive sensor, a stress sensor, an ultrasonic transducer, or an electrical resistance sensor, each configured to collect data on the amount of pressure on the pressure sensor, which can indicate the level of contact of one or more portions of the at least one glove 102 with a subject. The pressure data can be collected and transmitted to the controller 106. The controller 106 can be configured to determine if the at least a portion of the at least one glove 102 was contacting the subject with a selected amount of pressure at the time that one or more measurements (e.g., electrical potential measurements or positional measurements) were made. In instances in which the at least one glove 102 was making sufficient contact with the subject, the controller 106 can be configured to tag or otherwise indicate that such measurements (e.g., electrical potential or acoustic measurements) were made with sufficient contact to ensure reliable results. In instances in which the at least one glove 102 was making insufficient contact with the subject when the measurement was taken, the controller 106 can be configured to tag or otherwise indicate that such measurements were made with insufficient contact and delete or otherwise segregate such data from calculations or determinations. For example, in an embodiment, the controller 106 can be configured to delete from the memory all electrical potential measurements taken when the corresponding pressure on an adjacent pressure sensor was below about 7 kPa, below about 35 kPa, below about 70 kPa, or outside the range of 7 kPa to about 140 kPa. Such pressure thresholds can ensure that the corresponding electrical potential measurements were taken when the at least one electrode 104 corresponding to the pressure sensor had sufficient contact to allow an accurate measurement of electrical potential.

In an embodiment, the at least one position sensor 130 can be communicably coupled to the controller 106 (e.g., via the receiver 118). For example, the at least one position sensor 130 can be wiredly or wirelessly coupled to the controller 106. In an embodiment, the at least one position sensor 130 can communicate the detected one or more positions of at least one electrode 104 to the controller 106. The controller 106 can then store the detected one or more positions of the at least one electrode 104 in the memory 108. The processor 110 can then use the detected one or more positions of the at least one electrode 104 to facilitate the operation of the EKG system 100.

In an embodiment, the processor 110 can use the detected one or more positions of the at least one electrode 104 to minimize or prevent artifacts detected by the at least one electrode 104. An artifact can be caused by body features of the subject or devices at least proximate to the subject that electrically interferes with the electrical potential detected by the at least one electrode 104. Sources of artifacts include a surface above a bone, a surface proximate to a moving muscle, or an implanted medical device (e.g., pace maker). In an embodiment, the at least one position sensor 130 can detect possible sources of artifacts. The controller 106 can direct an individual using the at least one glove 102 away from any surfaces likely to cause artifacts, for example, using the user interface 124. For example, the user interface 124 can indicate position of the at least one electrode 104 relative to surface likely to cause artifacts. In an embodiment, the memory 108 can include a database of reference data that includes one or more biological structures of the subject. The one or more biological structures can be any biological structure that can be detected by the at least one position sensor 130 and can serve as one or more reference points to determine the position of the at least one electrode 104 relative to the subject. For example, the reference data stored on the memory 108 can include an anatomical map. The anatomical map can be an anatomical map of the subject generated from a previous medical procedure (e.g., x-ray, CAT scan, etc.), an anatomical map of another person, or an anatomical map of a generic person. The anatomical map of the subject can includes one or more features that the at least one position sensor 130 can detect (e.g., surface topography, internal features, etc.). The processor 110 can use the anatomical map to identify surfaces likely to cause artifacts or the anatomical map of the subject can identify such surfaces.

In an embodiment, the processor 110 can use the detected one or more positions of the at least one electrode 104 to direct an individual using the at least one glove 102 to contact the at least one electrode 104 against one or more preferred surfaces of the subject or a surface having one or more preferred surface characteristics. The one or more preferred surfaces of the subject can be any surface that enables the EKG system 100 to measure certain angles or anatomical areas of the heart. The one or more preferred surface characteristics can be any characteristic of the one or more preferred surfaces (e.g., a surface having a certain position relative to the heart). In an embodiment, the one or more preferred surfaces or the one or more preferred surface characteristics can be stored in the memory 108. For example, the memory 108 can include an anatomical map and the anatomical map can include the one or more preferred surfaces. In an embodiment, an individual can upload one or more preferred surfaces or one or more preferred surface characteristics into the memory 108 using the user interface 124. Alternatively, the one or more preferred surfaces or one or more preferred surface characteristics can be already stored in the memory 108. In an embodiment, the one or more preferred surfaces can be one or more of the surfaces used in a 3 lead wire EKG system, a standard 5 lead EKG system using lead $V_1$, a standard 5 lead EKG system using lead $V_5$, the EASI™ lead system, an interpolated 12 lead EKG cardiac monitoring system, or a typical 12 lead EKG. In an embodiment, the one or more preferred surfaces can be any two or more surfaces selected to measure certain angles or anatomical areas of the heart.

In an embodiment, the processor 110 can use the detected positions of the at least one electrode 104 to generate the report. For example, the at least one electrode 104 can measure a first electrical potential at a first surface of the subject and a second electrical potential at a second surface of the subject. The at least one position sensor 130 can detect the position of the first surface and the second surface relative to the subject. In an embodiment, the processor 110 can include the detected positions of the first surface and the second surface in the report. In an embodiment, the processor 110 can use the detected positions of the first surface and the second surface to determine an angle or anatomical area of the heart measured by the voltage between the detected first electrical potential and the detected second electrical potential.

In an embodiment, the user interface 124 can be configured to provide an indication that facilitates placement of the at least one electrode 104. For example, the indication provided by the user interface 124 can direct an individual using the at least one glove 102 to contact the at least one electrode 104 against a suitable surface. A suitable surface can be any surface that minimizes artifacts, the one or more preferred surfaces, or exhibits one or more preferred surface characteristics.

In an embodiment, the user interface 124 can be configured to provide an audio indication. As such, the user interface 124 can include one of more devices configured to output the audio indication (e.g., a speaker, a piezoelectric). The audio indication can include one or more tones outputted by the user interface 124 configured to convey the position or proximity of the at least one electrode 104 relative to a suitable surface. For example, the one or more tones can chime at short intervals when the at least one electrode 104 is proximate or closer to a suitable surface and can chime at longer intervals when the at least one electrode 104 is remote or farther from the suitable surface, or vice versa. In an embodiment, the one or more tones can increase volume when the at least one electrode 104 is proximate or closer to a suitable surface and can decrease volume when the at least one electrode 104 is remote or farther from the suitable surface, or vice versa. In another example, the one or more tones can output a first tone (e.g., one or more specific notes) when the at least one electrode 104 is proximate or closer to a suitable surface and a second tone when the at least one electrode 104 is remote or farther from the suitable surface, or vice versa.

In an embodiment, the user interface 124 can be configured to provide a visual indication. As such, the user interface 124 can be configured to include one of more devices configured to emit the visual indication (e.g., a display, at least one light emitting diode (LED)). For example, the visual indication can include one or more lights (e.g., LEDs) outputted by the user interface 124 configured to convey the position or proximity of the at least one electrode 104 towards a suitable surface (e.g., the one or more preferred surfaces). For instance, the one or more lights can flash at short intervals when the at least one electrode 104 is proximate or closer to a suitable surface and can flash at longer intervals when the at least one electrode 104 is remote or farther from the suitable surface, or vice versa. In an embodiment, the one or more lights can increase in intensity when the at least one electrode 104 is proximate or closer to a suitable surface and can decrease in intensity when the at least one electrode 104 is remote or farther from the suitable surface, or vice versa. In another instance, the one or more tones can output a first color when the at least one electrode 104 is proximate or closer to a suitable surface and a second color when the at least one electrode 104 is remote or farther from the suitable surface, or vice versa. In an embodiment, the one or more lights can indicate a direction that the at least one electrode 104 needs to move relative to the suitable surface. For instance, if the at least one electrode 104 needs to move to the left, the one or more lights on a left portion of the at least one glove can flash, increase intensity, or exhibit a certain color.

In an embodiment, the user interface 124 can be configured to provide a tactile indication to the user. For example, a tactile indication device can be provided, which includes one or more tightening mechanisms incorporated into the at least one glove 102. The one or more tightening mechanisms can tighten at least a portion of the at least one glove 102 around a hand of an individual using the at least one glove 102 when the at least one electrode 104 is proximate or closer to a suitable surface and can loosen at least a portion of the glove when the at least one electrode 104 is remote or farther from the suitable surface, or vice versa. In an embodiment, the tactile indication device can include one or more vibrating elements incorporated into the at least one glove 102. The one or more vibrating elements can vibrate at least a portion of the at least one glove 102. The one or more vibrating elements can vibrate at shorter intervals or stronger intensities when the at least one electrode 104 is proximate or closer to a suitable surface and can vibrate at longer intervals or weaker intensities when the at least one electrode 104 is remote or farther from the suitable surface, or vice versa. In an embodiment, the tactile indication device can include one or more selectively deployable nodes incorporated into the at least one glove 102. The one or more selectively deployable nodes can selectively deploy when the at least one electrode 104 is proximate or closer to a suitable surface and can selectively un-deploy when the at least one electrode 104 is remote or farther from the suitable surface, or vice versa. In an embodiment, the one or more tightening mechanisms, one or more vibrating elements, or one or more selectively deployable nodes can indicate a direction that the at least one electrode 104 needs to move relative to the suitable surface. For instance, if the at least one electrode 104 needs to move to the left, the one or more tightening mechanisms on a left portion of the at least one glove can tighten.

In an embodiment, the EKG system 100 can include a contact sensor 132. The contact sensor 132 can determine a quality of the electrical contact between a surface of the subject and at least one electrode 104. In an embodiment, the at least one contact sensor 132 can analyze the electrical potential detected by the at least one electrode 104 to determine the contact quality. In an embodiment, the at least one contact sensor 132 can include a sensor configured to determine a percentage of the at least one electrode 104 that contacts a surface, detect the presence of hair or other obstructions on the surface that can affect the electrical contact between the at least one electrode 104 and a surface, or detect the presence of a conductive gel on the surface of the at least one electrode 104 or the surface. In an embodiment, the processor 110 or another component of the controller 106 can perform the function of the contact sensor 132.

Figure 3:
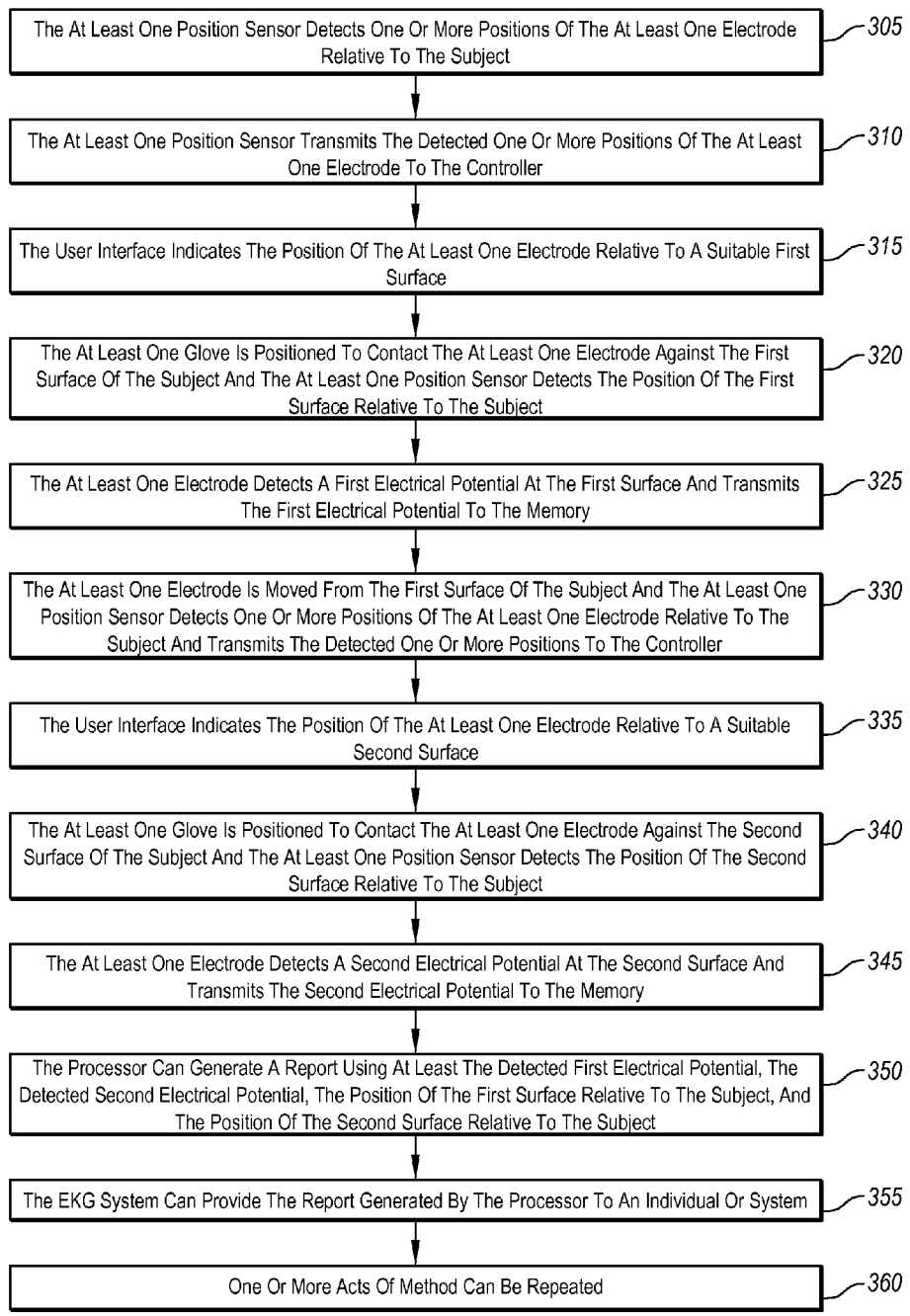
FIG. 3 is a flow diagram of a method of using the EKG system shown in FIG. 1, according to an embodiment.

FIG. 3 is a flow diagram of another method 300 of using the EKG system 100 shown in FIG. 1, according to an embodiment. The acts of the method 300 can be performed in any order. In an embodiment, some of the acts of the method 300 can be split into a plurality of acts, some of the acts can be combined into a single act, and some acts can be omitted. Also, it is understood that additional acts can be added to the method 300. For example, additional acts can be required to operate other EKG systems disclosed herein.

In act 305, the at least one position sensor 130 can detect one or more positions of the at least one electrode 104 relative to the subject. In an embodiment, the at least one position sensor 130 can detect the one or more positions of the at least one electrode 104 responsive to direction from the control electrical circuitry 116. For example, the control electrical circuitry 116 can direct the at least one position sensor 130 to substantially continuously detect the position of the at least one position sensor 130. In an embodiment, the control electrical circuitry 116 can direct the at least one position sensor 130 to detect the position of the at least one electrode 104 at certain times. In an embodiment, the at least one position sensor 130 can detect the one or more positions of the at least one electrode 104 without receiving direction from the control electrical circuitry 116. For example, the at least one position sensor 130 can detect the position of the at least one electrode 104 substantially continuously, at certain times preprogrammed into the at least one position sensor 130, when the at least one glove 102 is moving (e.g., the at least one glove 102 includes a motion sensor), or when a hand is positioned within the at least one glove 102.

In act 310, the at least one position sensor 130 can transmit the detected one or more positions of the at least one electrode 104 to the controller 106. In an embodiment, the at least one position sensor 130 transmits the detected one or more positions directly or indirectly to the controller 106. For example, the at least one position sensor 130 can transmit the detected one or more positions to the receiver 118 or to the memory 108. The at least one position sensor 130 can transmit the detected one or more positions concurrent with detecting the one or more positions or at some time period after detecting the one or more positions.

In act 315, the user interface 124 can indicate the position of the at least one electrode 104 relative to a suitable first surface. In an embodiment, the processor 110 uses the detected one or more positions of the at least one electrode 104 to determine the position of the at least one electrode 104 relative to a suitable surface. The control electrical circuitry 116 can direct the user interface 124 to indicate the position of the at least one electrode 104 relative to the suitable surface. For example, the user interface 124 can indicate when the at least one electrode 104 is at or near the suitable surface, when the at least one electrode 104 is spaced from the suitable surface, a direction to move the at least one electrode 104, or any other suitable means to indicate the position of the at least one electrode 104 relative to the suitable surface. The user interface 124 can indicate the position of the at least one electrode 104 relative to the suitable surface using an audio indication, a visual indication, or a tactile indication device.

In act 320, the at least one glove 102 can be positioned to contact the at least one electrode 104 against the first surface of the subject and the at least one position sensor 130 detects the position of the first surface relative to the subject. The at least one position sensor 130 can transmit the position of the first surface to the controller 106. The controller 106 can store the position of the first surface in the memory 108. In an embodiment, the at least one glove 102 includes a plurality of electrodes 104. In such an embodiment, one or more of the plurality of electrodes 104 can contact one or more surfaces of the subject. The at least one position sensor 130 can detect the position of the one or more of the surfaces contacted by the plurality of electrodes 104.

In act 325, the at least one electrode 104 can detect a first electrical potential detected at the first surface and transmits the first electrical potential to the memory 108. The at least one electrode 104 can detect the first electrical potential in substantially the same manner as described in act 210 of FIG. 2. Additionally, the at least one electrode 104 can transmit the first electrical potential to the memory 108 in substantially the same manner as described in act 215 of FIG. 2.

In act 330, the at least one electrode 104 is moved from the first surface of the subject and the at least one position sensor 130 detects one or more positions of the at least one electrode 104 relative to the subject and transmits the detected one or more positions to the controller 106. The at least one position sensor 130 can detect the one or more positions relative to the one or more positions previously detected in act 305, or can detect the motion associated with the change in position of electrode 104 from that detected in act 305. The at least one position sensor 130 can detect the one or more positions and transmit the detected one or more positions in substantially the same manner as described in acts 305 and 310, respectively. In act 335, the user interface 124 indicates the position of the at least one electrode 104 relative to a suitable second surface. The user interface 124 can indicate the position of the at least one electrode 104 in substantially the same manner as described in act 315. In act 340, the at least one glove 102 is positioned to contact the at least one electrode 104 against the second surface of the subject and the at least one position sensor 130 detects the position of the second surface relative to the subject. The at least one glove 102 is positioned and the at least one position sensor 130 detects the position of the second surface in substantially the same manner as described in act 320. In act 345, the at least one electrode detects a second electrical potential at the second surface and transmits the second electrical potential to the memory 108. The at least one electrode detects the second electrical potential and transmits the second electrical potential to the memory 108 is substantially the same manner as described in act 325.

In act 350, the processor 110 can generate a report using at least the detected first electrical potential, the detected second electrical potential, the position of the first surface relative to the subject, and the position of the second surface relative to the subject. The report can include a graphical representation of the voltage between the detected first electrical potential and the detected second electrical potential as a function of time. The report can also include the detected position of the first surface and the detected position of the second surface. In an embodiment, the processor 110 can compare the detect position of the first surface and the detected position of the second surface to determine which angle or anatomical area of the heart is measured by the voltage. In an embodiment, the detected first electrical potential and the detected second electrical potential can be used to form a composite electrical potential. The processor 110 can compare the detected position of the first surface and the detect position of the second surface to determine a hypothetical composite surface. In an embodiment, the processor 110 can generate the report in substantially the same manner as described in act 240 shown in FIG. 2.

In act 355, the EKG system 100 can provide the report generated by the processor 110 to an individual or system. For example, the EKG system 100 can transmit the report to the user interface 124 which displays the report using the display 126.

In act 360, one or more acts of method 300 can be repeated. For example, acts 305 to 325 can be repeated to detect the one or more additional electrical potentials (e.g., a third electrical potential) at one or more additional surfaces (e.g., a third surface) of the subject.

Figure 4:
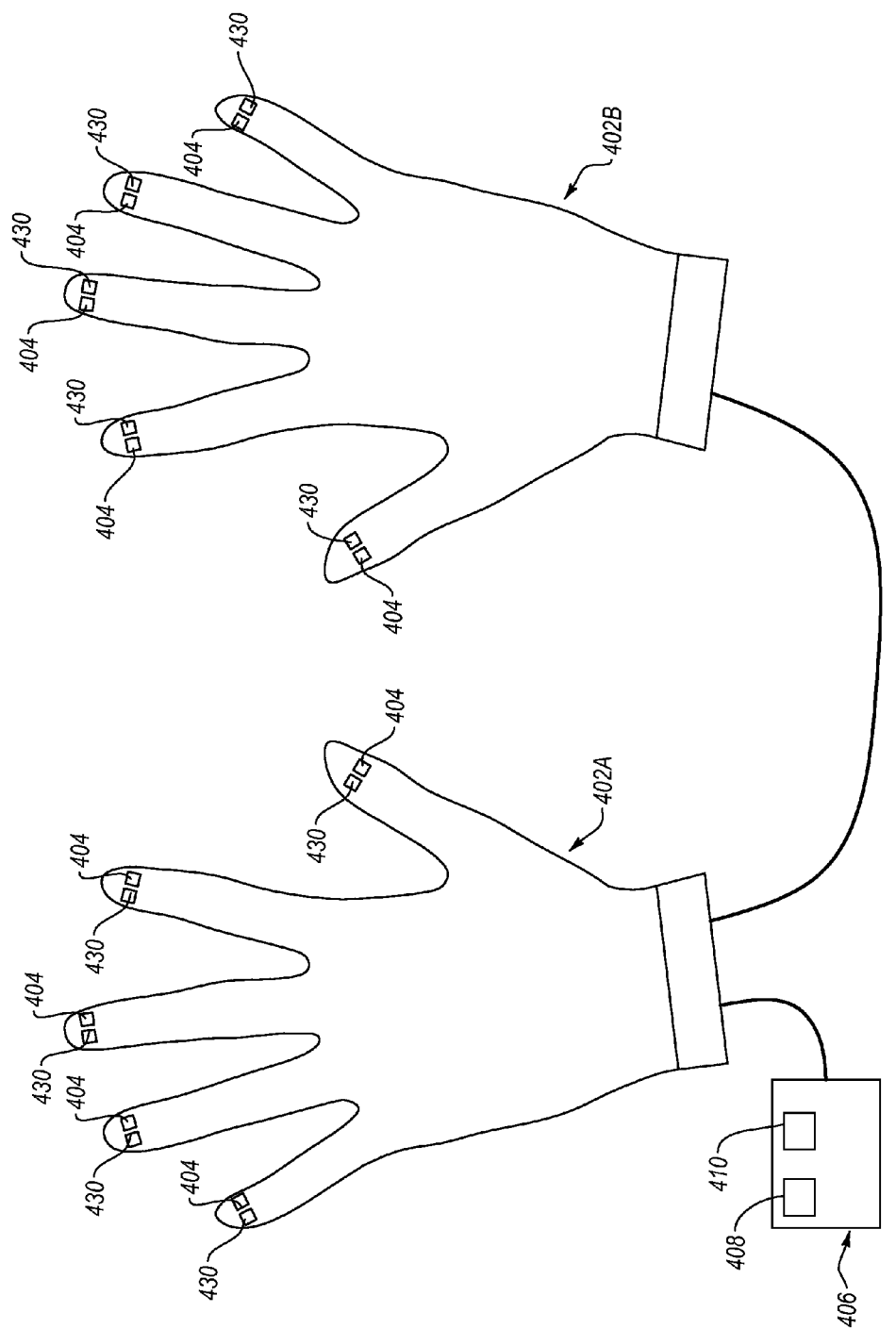
FIG. 4 is a schematic illustration of an EKG system, according to an embodiment.

FIG. 4 is a schematic illustration of an EKG system 400, according to an embodiment. The EKG system 400 includes a first glove 402A (e.g., a right-handed glove) and a second glove 402B (e.g., a left-handed glove). The first glove 402A and the second glove 402B can each include at least one electrode 404. The at least one electrode 404 is configured to detect two or more electrical potentials at two or more surfaces at different times. Additionally, the first glove 402A and the second glove 402B can each include at least one position sensor 430 configured to determine one or more positions of the at least one electrode 404 relative to the subject. Each of the at least one electrode 404 and the at least one position sensor 430 is communicably coupled to a controller 406. The controller 406 can include memory 408 and a processor 410.

In an embodiment, each of the first glove 402A and the second glove 402B are substantially the same. In an embodiment, the first glove 402A and the second glove 402B are different. For example, the first glove 402A and the second glove 402B can be different types of gloves. For instance, the first glove 402A can include fingers 414 and each finger 414 includes at least one electrode 404 positioned therein while the second glove 402B does not include any fingers and only includes an electrode 404 positioned in the palm 412. In an embodiment, the first glove 402A and the second glove 402B can include different electrodes 404 therein (e.g., more precise electrodes, skin piercing electrodes) or different position sensors 430 therein (e.g., an optical sensor, an acoustic sensor). In an embodiment, the first glove 402A or the second glove 402B can include at least a portion of the controller 406 positioned therein.

The first glove 402A and the second glove 402B can measure two or more electrical potentials at two or more different surfaces substantially simultaneously or substantially non-simultaneously. In an embodiment, at least one electrode 404 of the first glove 402A can contact a first surface of the subject and at least one electrode 404 of the second glove 402B can contact a third surface of the subject. The at least one position sensor 430 can also detect the relative positions of the first and third surfaces relative to the subject. The at least one electrode 404 of the first glove 402A can detect a first electrical potential at the first surface and the at least one electrode 404 of the second glove 402B can detect a third electrical potential at the second surface. The first glove 402A and the second glove 402B can transmit the detected first electrical potential and the detected third electrical potential, respectively, to the memory 408. In an embodiment in which the first glove 402A and the second glove 402B detect the first electrical potential and the third electrical potential substantially simultaneously, the processor 410 can determine the voltage between the detected first electrical potential and the detected third electrical potential while the first glove 402A and the second glove 402B detect the first and third electrical potentials, respectively. Alternatively, the processor 410 can determine the voltage between the detected first electrical potential and the detected third electrical potential after first and third electrical potentials are detected. After the first and third electrical potentials are detected, the at least one electrode of the first glove 402A can contact a second surface of the subject and the at least one electrode of the second glove 402B can contact a fourth surface of the subject. The second surface and the fourth surface can be the same as, adjacent to, proximate to, or distinct from the first surface or the third surface. The at least one position sensor 430 of the first glove 402A and the second glove 402B can detect the relative position of the second and fourth surfaces relative to the subject. The at least one electrode 404 of the first glove 402A can detect a second electrical potential at the second surface and the at least one electrode 404 of the second glove 402B can detect a fourth electrical potential at the fourth surface. The first glove 402A and the second glove 402B can transmit the detected second electrical potential and the detected fourth electrical potential, respectively, to the controller 406. The controller 406 can determine the voltage between the detected second and fourth electrical potentials while the first glove 402A and the second glove 402B detects both electrical potentials, or at some time period after both electrical potentials are detected. After the second and fourth electrical potentials are detected and transmitted to the controller 406, the processor 410 can determine the voltage between the detected second electrical potential and the detected first electrical potential, the detected second electrical potential and the detected third electrical potential, the detected fourth electrical potential and the detected first electrical potential, or the detected fourth electrical potential and the detected third electrical potential. In an embodiment, the first glove 402A and the second glove 402B can be positioned to detect additional electrical potentials at additional surfaces.

In an embodiment, the first glove 402A and the second glove 402B can be communicably coupled together. For example, the first glove 402A can be wiredly or wirelessly coupled to the second glove 402B. In an embodiment, at least one of the first glove 402A or the second glove 402B includes a device (e.g., the receiver 118 or the transmitter 122 shown in FIG. 1A) that communicably couples the first glove 402A or the second glove 402B to a device or system that is remote therefrom. For example, the first glove 402A or the second glove 402B can be configured to connect to a cellular network, Wi-Fi, or another suitable communication network. In an embodiment, the first glove 402A and the second glove 402B can be configured to be communicably coupled to the controller 406. For example, in the illustrated embodiment, the first glove 402A is configured to be directly communicably coupled to the controller 406 while the second glove 402B is indirectly communicably coupled to the controller 406 through the first glove 402A.

In the illustrated embodiment, at least a portion of the controller 406 can be remote from the first glove 402A and the second glove 402B. For example, at least a portion of the controller 406 can be located proximate to the first glove 402A and the second glove 402B. Alternatively, at least a portion of the controller 406 can be located a significant distance from the first glove 402A and the second glove 402B. For example, at least a portion of the controller 406 can be located in a different room, a different building, a different city, or a different country. In such an example, the first glove 402A the second glove 402B can be configured to connect to a Wi-Fi network, LAN network, cellular network, or any suitable communication network. As such, the controller 406 can be used in telemedicine, that is, provide clinical health care at a distance. In an embodiment, the controller 406 can be at least partially positioned in the first glove 402A or the second glove 402B.

Figure 5:
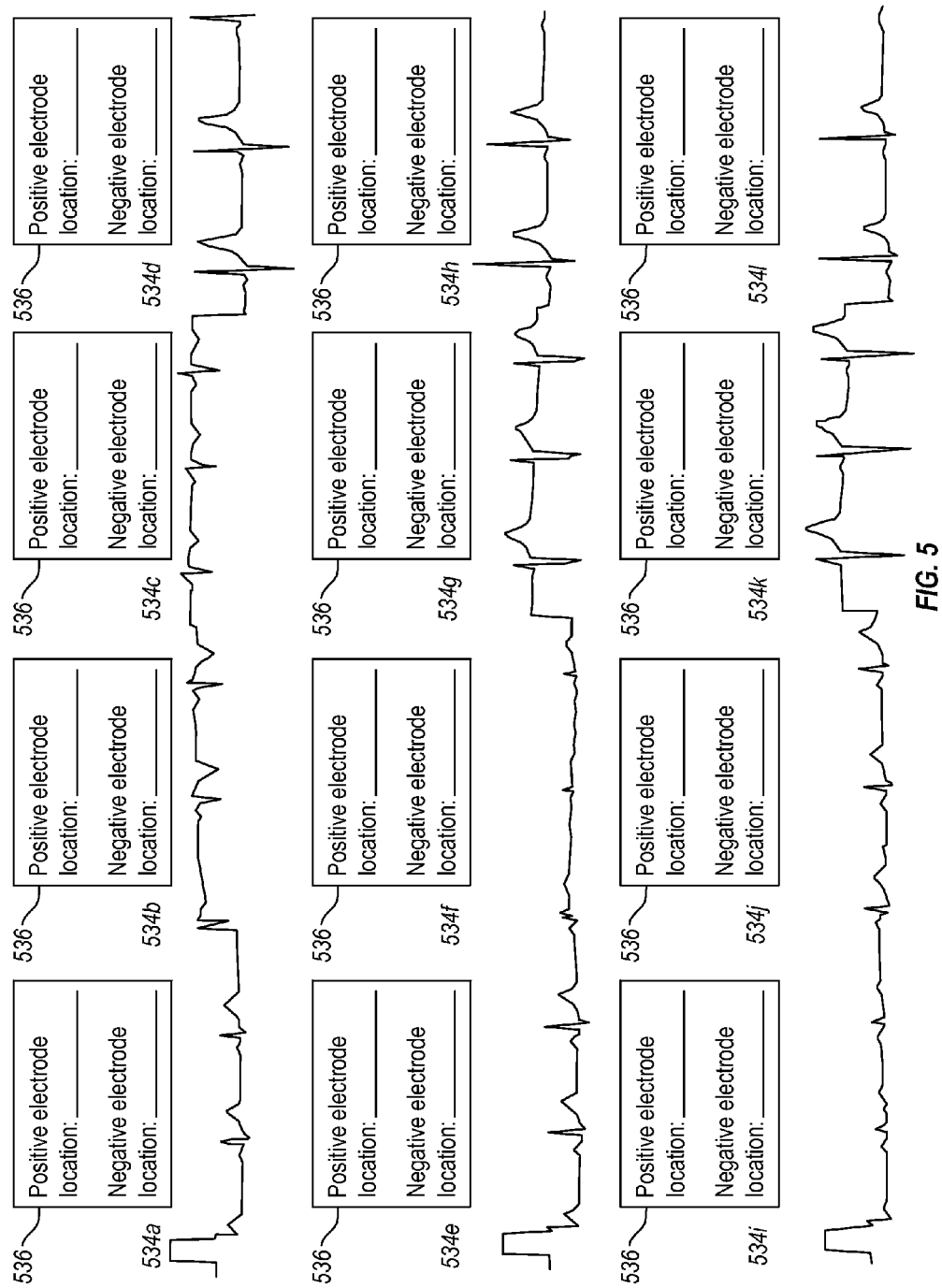
FIG. 5 is an illustration of a report generated by a processor of an EKG system, according to an embodiment.

FIG. 5 is an illustration of a report 532 generated by a processor (e.g., processor 110 shown in FIG. 1) of an EKG system, according to an embodiment. In an embodiment, the report 532 can include one or more graphical representations 534. Each graphical representation 534 can illustrate a voltage between two different electrical potentials detected at two different surfaces of the subject as a function of time. For example, the report can include a single graphical representation 534 or a plurality of graphical representations 534. In the illustrated embodiment, the report includes 12 graphical illustrations 534a to 534k.

The report 532 can include information therein that assists an individual interpret the report 532. For example, each graphical representation 534 can include an informational box 536 that includes information about each graphical representation 534. The information box 536 can include information that assists an individual interpret the report 532. In the illustrated embodiment, the information box 536 includes the position of the positive electrode (e.g., the position of a first surface relative to the subject) and the position of the negative electrode (e.g., the position of a second surface of the subject). The graphical representation 534 is generated by subtracting the electrical potential detected by the negative electrode from the electrical potential detected by the positive electrode. Such information can enable the individual to determine the angle or anatomical area of the heart measured by the illustrated voltage. The information box 536 can include additional information about each graphical representation 534, such as: when each electrical potential was detected, whether each electrical potential was detected once or a plurality of times, the time interval during which each electrical potential was detected, whether a composite electrical potential was used to generate a graphical representation 534, the position of the hypothetical composite surface relative to the subject, the position of each surface relative the subject for each electrical potential used to calculate the composite electrical potential, whether an interpolated electrical potential was used to generate a graphical representation, the target time used to predict the interpolated electrical potential, the association between the target time and a time C, whether an electrical potential was adjusted and how the electrical potential was adjusted, who operated the at least one glove, where (geographically) the EKG system was used, whether the subject had one or more devices implanted therein (e.g., pacemaker), whether one or more devices were proximate the subject, one or more characteristics detected by the at least one position sensor (e.g., the presence of bones proximate a surface), the type of EKG system used (e.g., one or more components of the EKG system), whether the electrical potential was detected while the EKG system simultaneously detected another electrical potential, the angle measured by the voltage, the anatomical area of the heart measured by the voltage, historical data of the subject, population data, whether historical data of the subject or population data was used to generate the graphical representation 534, or any other suitable information.

In an embodiment, the report 532 generated by the processor can include additional information attached thereto. For example, the report 532 can include historical data of the subject or population data attached thereto. The report 532 can include any information attached thereto that can assist an individual interpret the graphical representation 534.

Figure 6A:
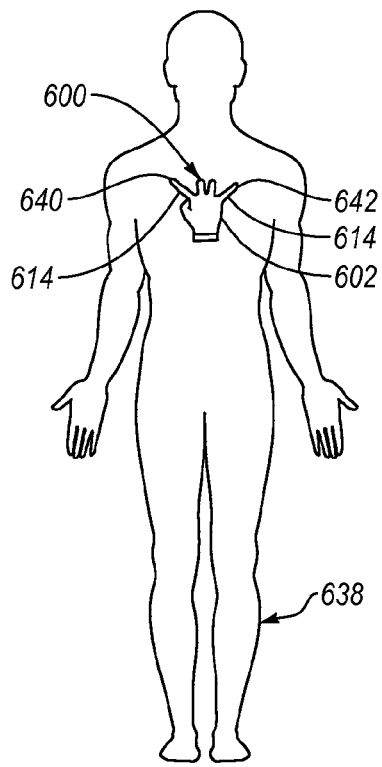
FIGS. 6A-6C are schematic illustrations of a method of using an EKG system to generate a 12 lead EKG report, according to an embodiment.
Figure 6B:
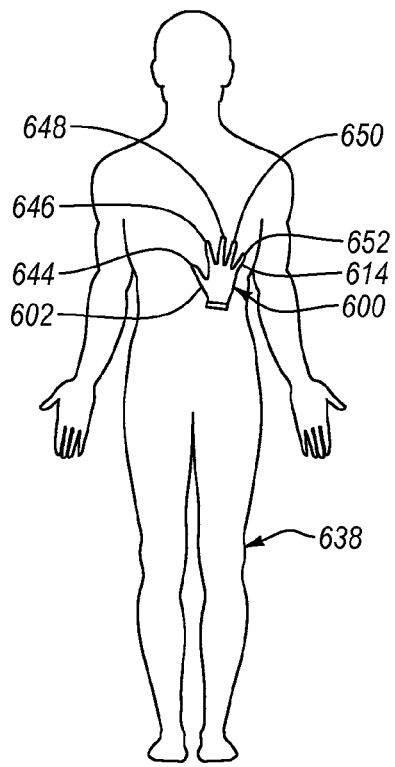
Figure 6C:
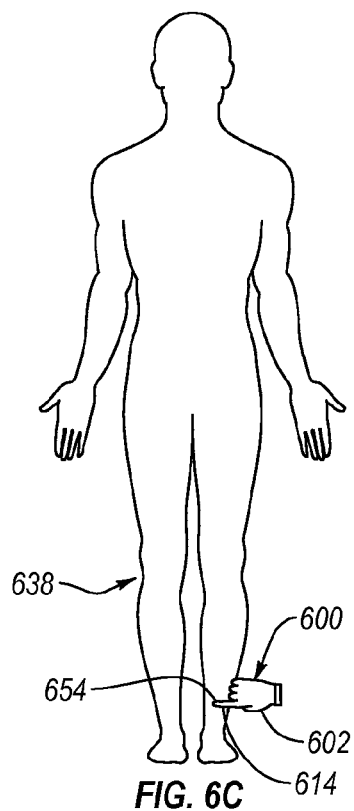

FIGS. 6A-6C are schematic illustrations of a method of using an EKG system 600 to generate a 12 lead EKG report, according to an embodiment. The EKG system 600 can include any of the EKG systems disclosed herein. For example, the EKG system 600 can include at least one glove 602. The at least one glove 602 can include a plurality of fingers 614. The at least one glove 602 can include least one electrode (not shown). For example, EKG system 600 can include at least one electrode positioned in each finger 614. The at least one glove 602 can also include at least one position sensor (not shown) configured to detect the position of the at least one electrode relative to the subject 638.

In FIG. 6A, the at least one glove 602 is positioned to contact at least one electrode against a first surface 640 of the subject 638 and at least one electrode against a second surface 642 of the subject 638. The first surface 640 and the second surface 642 can be located on the right arm (e.g., right shoulder) or left arm (e.g., left shoulder) of the subject, respectively, or the chest. In an embodiment, the at least one glove 602 includes a single glove 602. The single glove 602 can contact the first surface 640 and a second surface 642 substantially simultaneously if the single glove 602 is sufficiently large and the distance between the first surface 640 and the second surface 642 is sufficiently small. As such, the single glove 602 can detect a first electrical potential at the first surface 640 and a second electrical potential at the second surface 642 substantially simultaneously. Alternatively, the single glove 602 can contact at least one electrode against the first surface 640 and detect the first electrical potential at the first surface 640. After detecting the first electrical potential, the single glove 602 can contact at least one electrode against the second surface 642 and detect the second electrical potential at the second surface 642. In an embodiment, the at least one glove 602 can include two gloves, such as a first glove (not shown) and a second glove (not shown). The first glove can contact at least one electrode against the first surface 640 while the second glove contacts at least one electrode against the second surface 642. The first glove can detect a first electrical potential at the first surface 640 and the second glove can detect the second electrical potential at the second surface 642 substantially simultaneously or substantially non-simultaneously. In an embodiment, the at least one position sensor can detect the positions of the first surface 640 and the second surface 642 relative to the subject 638. Alternatively, the individual can upload the position of the first surface 640 and the second surface 642 into the EKG system 600 (e.g., using a user interface), or the EKG system 600 can assume that electrodes are correctly positioned.

In FIG. 6B, the at least one glove 602 is positioned to contact at least one electrode against a third surface 644, a fourth surface 646, a fifth surface 648, a sixth surface 650, and a seventh surface 652 of the subject 638. The third surface 644, the fourth surface 646, the fifth surface 648, the sixth surface 650, and the seventh surface 652 can be located on the chest of the subject and can correspond to five of the $V_1$, $V_2$, $V_3$, $V_4$, $V_5$, or $V_6$ chest electrode placement. In an embodiment, the at least one glove 602 can include a single glove 602 that contacts the third surface 644, the fourth surface 646, the fifth surface 648, the sixth surface 650, and the seventh surface 652 substantially simultaneously. As such, the single glove 602 can detect a third electrical potential at the third surface 644, a fourth electrical potential at the fourth surface 646, the a fifth electrical potential at fifth surface 648, a sixth electrical potential at the sixth surface 650, and a seventh electrical potential at the seventh surface 652 substantially simultaneously or substantially non-simultaneously. In an embodiment, the at least one glove 602 can include a first glove (not shown) and a second glove (not shown). The first glove and the second glove can contact one or more surfaces of the subject 638 that correspond to at least one of the six chest electrode placements, such as all six chest electrode placements. In an embodiment, the at least one position sensor can detect the positions of the third surface 644, the fourth surface 646, the fifth surface 648, the sixth surface 650, and the seventh surface 652 relative to the subject 638. Alternatively, the individual can upload the position of the third surface 644, the fourth surface 646, the fifth surface 648, the sixth surface 650, and the seventh surface 652 into the EKG system 600 (e.g., using a user interface), or the EKG system 600 can assume that the electrodes are correctly positioned.

In FIG. 6C, the at least one glove 602 is positioned to contact at least one electrode against an eighth surface 654 of the subject 638. The eighth surface 654 can be on the left leg of the subject. The at least one electrode can detect an eighth electrical potential at the eighth surface 654. In an embodiment, the at least one position sensor can detect the positions of the eighth surface 654 relative to the subject 638. Alternatively, the individual can upload the position of the eighth surface 654 into the EKG system 600 (e.g., using a user interface), or the EKG system 600 can assume that the at least one electrodes is correctly positioned.

The EKG system 600 can then compare the detected first electrical potential, the detected second electrical potential, the detected third electrical potential, the detected fourth electrical potential, the detected fifth electrical potential, the detected sixth electrical potential, the detected seventh electrical potential, the detected eighth electrical potential, or one or more additional electrical potentials (e.g., an additional electrical potential detected at the chest of the subject 638) to generate a report that includes at least 12 leads (i.e., voltages measured between 12 different angles). Some of the 12 leads can be generated from a composite electrical potential generated from one or more detected electrical potentials.

In an embodiment, the at least one glove 602 can include a first glove (not shown) and a second glove (not shown). In such an embodiment, the first glove and the second glove can detect electrical potentials at two distinct surfaces substantially simultaneously. For example, the first glove can contact the first surface 640 and the second surfaced 642 while the second glove contacts the eighth surface 654. Alternatively, the first glove can contact at least one surface shown in FIG. 6B while the second glove contacts at least one surface shown in FIG. 6A or FIG. 6C.

FIGS. 7A and 7B are schematic illustrations of a method of using an EKG system 700 to generate a report, according to an embodiment. The EKG system 700 can include any EKG system disclosed herein. For example, the EKG system 700 can include at least one glove 702. For example, the at least one glove 702 can include at least one finger 714. The at least one glove 702 can include at least one electrode (not shown). For example, the at least one electrode can be positioned in the at least one finger 714. The at least one glove 702 can also include at least one position sensor (not shown) configured to detect the position of the at least one electrode relative to the subject 638. In an embodiment, the EKG system 700 can be configured to detect one or more electrical potentials at one or more random surfaces of the subject 738.

In FIG. 7A, the at least one glove 702 is positioned to contact at least one electrode against a first surface 740 of the subject 738. The first surface 740 can be any surface on the subject 738. For example, the first surface 740 can be proximate the heart of the subject 738 (e.g., the chest), at or near a limb of the subject (e.g., an arm or leg of the subject), or any other location on the subject. In the illustrated embodiment, the first surface 740 is on the left arm of the subject 738. The at least one electrode can detect a first electrical potential at the first surface 740. In an embodiment, the at least one position sensor can detect the position of the first surface 740 relative to the subject 738. Alternatively, the individual can upload the position of the first surface 740 into the EKG system 700 (e.g., using a user interface).

In FIG. 7B, the at least one glove 702 is positioned to contact at least one electrode against a second surface 642 of the subject 738. The second surface 742 can be any surface on the subject 738. For example, the second surface 742 can be on a surface that is spaced from the first surface 740, such as on a distinctly different body part of the subject 738. In the illustrated embodiment, the second surface 742 is positioned on the right side of the chest of the subject 738. The at least one electrode can detect a second electrical potential at the second surface 742. In an embodiment, the at least one position sensor can detect the position of the second surface 742 relative to the subject 738. Alternatively, the individual can upload the position of the second surface 742 into the EKG system 700 (e.g., using a user interface).

The EKG system 700 can then compare the detected first electrical potential with the second electrical potential to generate a report. The report can include a graphical representation of the voltage between the detected first electrical potential and the detected second electrical potential as a function of time. The EKG system 700 can provide the position of the first surface 740 and the position of the second surface 742, relative to the subject 738, on the report. Alternatively, the EKG system 700 can calculate the angle or anatomical area of the heart measured by the voltage between the first electrical potential and the second electrical potential.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein can be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electrical systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context can dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

This disclosure has been made with reference to various example embodiments. However, those skilled in the art will recognize that changes and modifications may be made to the embodiments without departing from the scope of the present disclosure. For example, various operational acts, as well as components for carrying out operational acts, may be implemented in alternate ways depending upon the particular application or in consideration of any number of cost functions associated with the operation of the system; e.g., one or more of the acts may be deleted, modified, or combined with other acts.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational acts to be performed on the computer or other programmable apparatus to produce a computer-implemented process, such that the instructions that execute on the computer or other programmable apparatus provide acts for implementing the functions specified.

In an embodiment, the EKG systems disclosed herein can be integrated in such a manner that the EKG systems operate as a unique system configured specifically for detecting electrical potentials, and any associated computing devices of the EKG systems operate as specific use computers for purposes of the claimed system, and not general use computers. In an embodiment, at least one associated computing device of the EKG systems operates as a specific use computer for purposes of the claimed system, and not a general use computer. In an embodiment, at least one of the associated computing devices of the EKG systems is hardwired with a specific ROM to instruct the at least one computing device. In an embodiment, one of ordinary skill in the art recognizes that the EKG systems effects an improvement at least in the technological field of electrocardiograms.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A method of using an electrocardiogram system, the method comprising:
   contacting a first surface of a subject with at least one electrode of at least one glove that is worn by an individual other than the subject;
   with the at least one electrode, detecting a first electrical potential on the first surface of the subject;
   storing the detected first electrical potential in memory;
   after storing the detected first electrical potential in the memory, contacting a second surface of the subject with the at least one electrode of the at least one glove;
   with the at least one electrode, detecting a second electrical potential on the second surface of the subject;
   storing the detected second electrical potential in the memory; and
   with a processor, determining a voltage between the detected first electrical potential and the detected second electrical potential.

2. The method of claim 1, wherein:
   detecting the first electrical potential on the first surface of the subject includes detecting a plurality of first electrical potentials on the first surface of the subject; and
   storing the detected first electrical potential in the memory includes storing at least some of the detected plurality of first electrical potentials in memory.

3. The method of claim 2, further including, with the processor:
   selecting an antecedent first electrical potential and a subsequent first electrical potential from the detected plurality of first electrical potentials, wherein the at least one electrode detects the antecedent first electrical potential at an antecedent time and the subsequent first electrical potential at a subsequent time;
   selecting a target time, the target time between the antecedent time and the subsequent time; and
   predicting an interpolated first electrical potential at the target time, the interpolated first electrical potential is predicted based on the antecedent first electrical potential and the subsequent first electrical potential.

4. The method of claim 3, wherein selecting a target time includes:
   determining another time, the another time when the detected second electrical potential is detected by the at least one electrode or an interpolated second electrical potential at least partially predicted from the detected second electrical potential is detected; and
   selecting the target time to be substantially the same as or a specified number of heartbeats before or after the another time.

5. The method of claim 1, wherein:
   detecting the second electrical potential on the second surface of the subject includes detecting a plurality of second electrical potentials on the second surface of the subject; and
   storing the detected second electrical potential in the memory includes storing at least some of the detected plurality of second electrical potentials in memory.

6. The method of claim 5, further including, with the processor:
   selecting an antecedent second electrical potential and a subsequent second electrical potential from the detected plurality of second electrical potentials, wherein the at least one electrode detected the antecedent second electrical potential at an antecedent time and the subsequent second electrical potential at a subsequent time;
   selecting a target time, the target time between the antecedent time and the subsequent time; and
   predicting an interpolated second electrical potential detected at the target time, the interpolated second electrical potential is predicted based on the antecedent second electrical potential and the subsequent second electrical potential.

7. The method of claim 6, wherein selecting a target time includes:
   determining another time, the another time when the detected first electrical potential is detected by the at least one electrode or an interpolated first electrical potential at least partially predicted from the detected first electrical potential is detected; and
   selecting the target time to be substantially the same as or a specified number of heartbeats before or after the another time.

8. The method of claim 1, further including, with the processor, determining a heartbeat or a heart rate from the detected first electrical potential, the detected second electrical potential, or the voltage between the detected first electrical potential and the detected second electrical potential.

9. The method of claim 1, wherein contacting a second surface of the subject with the at least one electrode of the at least one glove includes contacting a surface of the subject with the at least one electrode that is on a distinctly different portion of the subject than the first surface.

10. The method of claim 1, further including,
    after storing the detected second electrical potential in the memory, contacting a third surface of the subject with the at least one electrode of the at least one glove;
    with the at least one electrode, detecting a third electrical potential on the third surface of the subject; and
    storing the detected third electrical potential in the memory.

11. The method of claim 10, further including,
with the processor, determining a composite electrical potential from an average electrical potential of two of the detected first, second, or third electrical potentials; and
with the processor, determining a voltage between the composite electrical potential and the detected first, second, or third electrical potentials that was not used to determine the composite electrical potential.

12. The method of claim 10, further including, with the processor, determining a voltage between the detected third electrical potential and at least one of the detected first electrical potential or the detected second electrical potential.

13. The method of claim 1, further including,
estimating an undetected electrical potential of a surface of the subject using at least one of historical data of the subject or population data; and
with the processor, determining a voltage between the undetected electrical potential and at least one of the detected first electrical potential or the detected second electrical potential.

14. The method of claim 1, wherein determining a voltage between the detected first electrical potential and the detected second electrical potential includes adjusting data associated with at least one of the detected first electrical potential or the detected second electrical potential to compensate for the detected first electrical potential and the detected second electrical potential being detected during different portions of a heartbeat of the subject or exhibiting different heart rates.

15. The method of claim 1, further including, with the processor, generating a report including the voltage determined between the detected first electrical potential and the detected second electrical potential.

16. The method of claim 15, further including comparing data of the report with at least one of historical data of the subject or population data to determine at least one characteristic of a heart of the subject.

17. The method of claim 1, further including, with at least one position sensor, detecting one or more positions of the at least one electrode relative to the subject.

18. The method of claim 17, wherein detecting one or more positions of the at least one electrode relative to the subject includes detecting a skin topography of a surface of the subject using the at least one position sensor.

19. The method of claim 17, wherein detecting one or more positions of the at least one electrode relative to the subject includes detecting bone or tissue density using the at least one position sensor.

20. The method of claim 17, wherein detecting one or more positions of the at least one electrode relative to the subject includes emitting and detecting sound waves to determine a position of the at least one electrode relative to the subject.

21. The method of claim 17, wherein detecting one or more positions of the at least one electrode relative to the subject includes detecting blood vessels using the at least one position sensor.

22. The method of claim 17, further including,
with the processor, comparing the detected one or more positions of the at least one electrode relative to the subject with one or more suitable surfaces stored on the memory, the one or more suitable surfaces include at least one of a surface that minimizes or prevents artifacts, one or more preferred surfaces, or one or more preferred surface characteristics;
with the processor, determining if the at least one electrode is at or near the one or more preferred surfaces; and
with a user interface of the electrocardiogram system, providing an indication regarding a position of the at least one electrode relative to the one or more suitable surfaces.

23. The method of claim 22, wherein providing an indication regarding a position of the at least one electrode relative to the one or more suitable surfaces includes at least one of providing an audio indication or providing a visual indication that the at least one electrode is at or near the one or more suitable surfaces.

24. The method of claim 23, wherein the visual indication includes one or more lights emitted from the user interface.

25. The method of claim 22, wherein providing an indication regarding a position of the at least one electrodes relative to the one or more suitable surfaces includes a tactile indication device including one or more of a tightening mechanism, a vibrating element, or a plurality of selectively deployable nodes.

26. The method of claim 25, wherein the user interface includes a tactile indication device including one or more of a tightening mechanism, a vibrating element, or a plurality of selectively deployable nodes.

27. The method of claim 17, further including, with the processor, generating a report including,
the voltage determined between the detected first electrical potential and the detected second electrical potential; and
the detected one or more positions of the at least one electrode relative to the subject.

28. The method of claim 1, further including, with a contact sensor, determining a quality of contact between the at least one electrode and at least one of the first surface or the second surface of the subject.

29. A system for capturing electrocardiogram readings, the system comprising:
at least one glove including at least one electrode, the at least one electrode configured to,
contact a first surface of a subject and detect a first electrical potential on the first surface; and
contact a second surface of the subject and detect a second electrical potential on the second surface at some time after the first electrical potential was detected;
wherein the at least one electrode is only positioned,
on or partially in an exterior surface of the at least one glove; or
in the at least one glove and positioned sufficiently proximate to the exterior surface of the at least one glove to detect a first electrical potential on the first surface of the subject when the exterior surface of the at least one glove contacts the first surface of the subject;
memory operably coupled to the at least one electrode, the memory configured to receive and store therein,
the detected first electrical potential; and
the detected second electrical potential; and
a processor operably coupled to the memory, the processor configured to,
determine a voltage between the detected first electrical potential and the detected second electrical potential; and
generate a report including the voltage.

30. The system of claim 29, wherein the at least one electrode is further configured to detect a plurality of first electrical potentials on the first surface.

31. The system of claim 30, wherein the processor is further configured to:
   select an antecedent first electrical potential and a subsequent first electrical potential from the detected plurality of first electrical potentials, wherein the at least one electrode detected the antecedent first electrical potential at an antecedent time and the subsequent first electrical potential as a subsequent time;
   select a target time between the antecedent time and the subsequent time; and
   predict an interpolated first electrical potential detected at the target time, the interpolated first electrical potential is predicted based on the antecedent first electrical potential and the subsequent first electrical potential.

32. The system of claim 31, wherein the processor is further configured to:
   determine an another time, the another time being when the detected second electrical potential is detected by the at least one electrode or an interpolated second electrical potential at least partially predicted from the detected second electrical potential is detected; and
   select the target time to be substantially the same as or a specified number of heartbeats before or after the another time.

33. The system of claim 29, wherein the at least one electrode is further configured to detect a plurality of second electrical potentials on the second surface.

34. The system of claim 33, wherein the processor is further configured to:
   select an antecedent second electrical potential and a subsequent second electrical potential from the detected plurality of second electrical potentials, wherein the at least one electrode detected the antecedent second electrical potential at an antecedent time and the subsequent second electrical potential as a subsequent time;
   select a target time between the antecedent time and the subsequent time; and
   predict an interpolated second electrical potential detected at the target time, the interpolated second electrical potential is predicted based on the antecedent second electrical potential and the subsequent second electrical potential.

35. The system of claim 29, wherein the processor is further configured to determine a heartbeat or heart rate from the detected first electrical potential, the detected second electrical potential, of the voltage.

36. The system of claim 29, wherein:
   the at least one electrode includes a plurality of electrodes; and
   the at least one glove includes a plurality of fingers each of which includes at least one of the plurality of electrodes therein or thereon.

37. The system of claim 36, wherein at least one of the plurality of electrodes is coupled to at least one of a distal phalanx, a middle phalanx, or a proximal phalanx of one of the plurality of fingers.

38. The system of claim 36, wherein at least one of the plurality of electrodes is coupled to a palm of the at least one glove.

39. The system of claim 29, wherein the at least one electrode is at least partially enclosed in the at least one glove.

40. The system of claim 29, wherein the at least one glove includes at least one position sensor configured to detect one or more positions of the at least one electrode relative to the subject.

41. The system of claim 40, wherein the at least one position sensor includes at least one optical sensor, the at least one optical sensor including a camera or an infrared detector.

42. The system of claim 40, wherein:
   the at least one position sensor includes a micro-impulse radar configured to detect one or more internal structures or one or more external structures of the subject; and
   the processor is further configured to determine a position of the at least one electrode relative to the subject at least partially based on the detected one or more internal structures or the detected one or more external structures.

43. The system of claim 40, wherein:
   the at least one position sensor includes at least one topography sensor configured to detect a skin topography of the first surface and the second surface of the subject; and
   the processor is further configured to determine a position of the at least one electrode relative to the subject at least partially based on the skin topography.

44. The system of claim 40, wherein:
   the at least one position sensor includes at least one acoustic sensor configured to detect a bone density or a tissue density of a surface of the subject using sound waves; and
   the processor is further configured to determine a position of the at least one electrode relative to the subject at least partially based on the detected bone density or the detected tissue density.

45. The system of claim 40, wherein:
   the at least one position sensor includes at least one sensor configured to detect blood vessels of a surface of the subject; and
   the processor is further configured to determine a position of the at least one electrode relative to the subject at least partially based on the detected blood vessels.

46. The system of claim 40, wherein the at least one glove includes at least one finger and the at least one position sensor is positioned in at least the at least one finger.

47. The system of claim 40, wherein the at least one glove includes a palm and the at least one position sensor is positioned in at least the palm of the at least one glove.

48. The system of claim 40, further including a user interface operably coupled to the processor, the user interface configured to indicate if the at least one electrode is positioned at or near one or more preferred surfaces of the subject for detecting electrical potential.

49. The system of claim 48, wherein
   the memory further includes the one or more preferred surfaces or one or more preferred surface characteristics stored therein;
   the processor is further configured to compare the one or more detected positions of the at least one electrode relative to the subject with the one or more preferred surfaces or one or more preferred surface characteristics and determine if the at least one electrode is at or near the one or more preferred surfaces; and
   the user interface is further configured to indicate if the at least one electrode is positioned at or near one or more preferred surfaces responsive to the comparison by the processor.

50. The system of claim 48, wherein the user interface includes one or more of a tightening mechanism, a vibrating elements, a selectively deployable nodes, a light affixed to a surface of the at least one glove, or an audible indicator configured to produce one or more tones.

51. The system of claim 40, wherein the processor is further configured to associate the detected first electrical potential and the detected second electrical potential with a corresponding one of the detected one or more positions of the at least one electrode.

52. The system of claim 40, wherein,
- the memory includes a database of reference data including biological structures capable of serving as reference points for determining a position of the at least one electrode relative to the subject; and
- the processor is further configured to compare the one or more detected positions of the at least one electrode detected by the at least one position sensor with the reference data in the database to determine the position of the at least one electrode relative the subject.

53. The system of claim 29, wherein:
- the memory includes at least one of historical patient data or population data stored thereon; and
- the processor is further configured to compare data of the report with at least one of the historical patient data or the population data.

54. The system of claim 29, wherein the at least one glove includes at least one contact sensor configured to determine the quality of the electrical contact between the at least one glove and a surface the subject.

* * * * *